US012521504B2

(12) United States Patent
Brady et al.

(10) Patent No.: US 12,521,504 B2
(45) Date of Patent: Jan. 13, 2026

(54) VACUUM SHIELD ASSEMBLY FOR ATTACHMENT TO MEDICAL MASKS

(71) Applicant: SafER Medical Products, LLC, Branson, MO (US)

(72) Inventors: Rob Brady, Sarasota, FL (US); Matt Vergin, St. Petersburg, FL (US); Barry Jennings, Largo, FL (US); Mike Winterhalter, Nokomis, FL (US); Richard Blubaugh, Branson West, MO (US); Craig Randall, Branson, MO (US); Misty Denevan, Branson, MO (US); Todd Baker, Walnut Shade, MO (US)

(73) Assignee: Safer Medical Products, LLC, Fircrest, WA (US)

( * ) Notice: Subject to any disclaimer, the term of this patent is extended or adjusted under 35 U.S.C. 154(b) by 714 days.

(21) Appl. No.: 17/191,823

(22) Filed: Mar. 4, 2021

(65) Prior Publication Data

US 2022/0072245 A1 Mar. 10, 2022

Related U.S. Application Data

(63) Continuation-in-part of application No. 17/173,724, filed on Feb. 11, 2021, now Pat. No. 12,083,273.

(Continued)

(51) Int. Cl.

| | |
|---|---|
| ***A61M 16/00*** | (2006.01) |
| ***A61M 16/06*** | (2006.01) |
| ***A61M 16/14*** | (2006.01) |

(52) U.S. Cl.

CPC .......... *A61M 16/009* (2013.01); *A61M 16/06* (2013.01); *A61M 16/14* (2013.01); *A61M 2202/0208* (2013.01)

(58) Field of Classification Search

CPC .......... A41D 13/11; A61B 90/57; A61M 1/28; A61M 1/76; A61M 1/84; A61M 1/15;

(Continued)

(56) References Cited

U.S. PATENT DOCUMENTS 3,067,425 A * 12/1962 Colley ................ A62B 18/086 137/614.19
3,136,515 A * 6/1964 Potruch .................... F16L 3/13 248/62

(Continued)

FOREIGN PATENT DOCUMENTS

CN 105797246 A 7/2016
CN 206007759 U 3/2017

(Continued)

OTHER PUBLICATIONS

International Search Report and Written Opinion for PCT/US2021/049619; Feb. 28, 2022; ISA-United States Patent and Trademark Office; entire document.

(Continued)

*Primary Examiner* — Brandy S Lee
(74) *Attorney, Agent, or Firm* — Allen, Dyer, Doppelt & Gilchrist, P.A.

(57) ABSTRACT

A vacuum shield assembly intended for attachment to an existing medical mask for air suction, nebulization, BIPAP, and/or CPAP. The vacuum shield assembly generally comprises a shield body and a retaining assembly. The retaining assembly may attach the vacuum shield assembly to a vacuum tube of the existing mask, which may be connected to a negative pressure vacuum. The retaining assembly may also be attached to a nebulizer unit or component thereof, or to an oxygen supply tube of a BIPAP or CPAP mask. The shield body may comprise a lower segment, which may comprise a connecting component configured and dimensioned for attachment to, and for a fluid communication, (Continued)

with the retaining assembly. The shield body may be configured and dimensioned to correspond to the geometry of the existing mask. As an example, the shield body may comprise a substantially concave configuration with a substantially semi-ovoidal edge.

16 Claims, 23 Drawing Sheets

Related U.S. Application Data

(60) Provisional application No. 63/075,890, filed on Sep. 9, 2020.

(58) Field of Classification Search
CPC ...... A61M 1/16; A61M 16/009; A61M 16/04; A61M 16/0415; A61M 16/0418; A61M 16/0434; A61M 16/0461; A61M 16/0463; A61M 16/0475; A61M 16/0477; A61M 16/0479; A61M 16/0486; A61M 16/0488; A61M 16/0493; A61M 16/0497; A61M 16/06; A61M 16/0666; A61M 16/0672; A61M 16/0683; A61M 16/08; A61M 16/0816; A61M 16/0875; A61M 2025/0057; A61M 2025/022; A61M 2025/0226; A61M 2025/024; A61M 2025/0253; A61M 2039/0009; A61M 2039/064; A61M 2039/087; A61M 2039/1027; A61M 2039/2426; A61M 2202/0413; A61M 2205/0272; A61M 2205/32; A61M 2209/08; A61M 2209/082; A61M 2209/088; A61M 2210/0618; A61M 2210/0625; A61M 2230/50; A61M 25/02; A61M 25/39; A61M 39/08; A61M 39/10; A61M 39/12; A61M 39/28; A61M 39/284; A61M 5/1418; A61M 11/06; A61M 16/14; A61M 2202/0208; A62B 18/086; Y10T 24/44; F16L 3/237; F16L 5/10
USPC ...................... 128/912; 604/167.04; 141/329
See application file for complete search history.

(56) References Cited

U.S. PATENT DOCUMENTS

| | | | | | |
|---|---|---|---|---|---|
| 3,432,129 | A * | 3/1969 | Santucci | F16L 3/237 | 248/69 |
| 4,219,020 | A * | 8/1980 | Czajka | A61M 16/0833 | 128/205.25 |
| 4,328,797 | A * | 5/1982 | Rollins, III | A61M 16/06 | 128/912 |
| 4,794,921 | A * | 1/1989 | Lindkvist | A61M 16/0833 | 128/203.29 |
| 4,798,594 | A * | 1/1989 | Hillstead | A61M 39/0606 | 604/167.04 |
| 4,807,617 | A * | 2/1989 | Nesti | A61M 16/06 | 128/203.29 |
| 4,895,172 | A * | 1/1990 | Lindkvist | A61M 16/0694 | 128/863 |
| 4,949,714 | A * | 8/1990 | Orr | A61M 16/0627 | 128/200.24 |
| 5,146,914 | A * | 9/1992 | Sturrock | A61M 16/06 | 128/202.29 |
| 5,263,671 | A * | 11/1993 | Baum | B62K 19/30 | 248/68.1 |
| 5,309,604 | A * | 5/1994 | Poulsen | F16L 3/223 | 24/339 |
| 5,311,862 | A * | 5/1994 | Blasdell | A61M 16/06 | 128/205.24 |
| 5,312,363 | A * | 5/1994 | Ryan | A61M 39/06 | 604/167.04 |
| 5,370,110 | A * | 12/1994 | Corn | A61M 16/0627 | 128/205.12 |
| 5,592,935 | A | 1/1997 | Elstran et al. | | |
| 5,653,411 | A * | 8/1997 | Picco | F16L 3/2235 | 24/339 |
| 5,676,133 | A | 10/1997 | Hickle | | |
| 5,871,011 | A * | 2/1999 | Howell | A61M 16/0093 | 128/911 |
| 6,106,030 | A * | 8/2000 | Nader | F16L 23/16 | 277/648 |
| 6,135,109 | A * | 10/2000 | Blasdell | A61M 16/06 | 128/206.28 |
| 6,263,874 | B1 * | 7/2001 | LeDez | A61M 16/085 | 128/205.25 |
| 6,364,257 | B1 * | 4/2002 | Holder | F16L 3/237 | 248/74.1 |
| 6,736,140 | B1 * | 5/2004 | Baczkowski | A61M 16/08 | 128/205.27 |
| 6,899,304 | B2 * | 5/2005 | Bellmore | F16L 3/1203 | 248/65 |
| 7,044,127 | B1 * | 5/2006 | Fernandez DeCastro | A41D 13/11 | 128/205.27 |
| 7,055,784 | B2 * | 6/2006 | Stigler | B60R 16/0215 | 248/68.1 |
| D598,537 | S * | 8/2009 | Nashed | A61M 16/06 | D24/110.4 |
| 7,647,928 | B2 * | 1/2010 | Muellinger | A61M 16/1065 | 128/206.29 |
| 8,291,905 | B2 * | 10/2012 | Moenning, Jr. | A61M 16/06 | 128/203.29 |
| 8,336,549 | B2 * | 12/2012 | Nashed | A61M 16/0605 | 128/203.29 |
| 8,479,625 | B2 * | 7/2013 | Klepper | A61M 16/0486 | 83/13 |
| 8,479,737 | B2 * | 7/2013 | Moenning, Jr. | A61M 16/06 | 128/203.29 |
| 8,539,953 | B2 * | 9/2013 | Moenning, Jr. | A61M 16/104 | 128/203.29 |
| 8,708,289 | B2 * | 4/2014 | Allenbach | F16L 3/2235 | 248/68.1 |
| 8,739,363 | B2 * | 6/2014 | Allen | A61B 50/20 | 16/2.2 |
| 8,826,905 | B2 * | 9/2014 | Nashed | A61M 16/0891 | 128/205.13 |
| 9,757,528 | B2 | 9/2017 | Rubin | | |
| 9,903,511 | B2 * | 2/2018 | Vermillion | F16L 3/1218 | |
| 10,070,743 | B2 * | 9/2018 | Sladics | A47G 19/2222 | |
| 10,188,814 | B2 * | 1/2019 | Moenning, Jr. | A61M 16/0816 | |
| 10,493,228 | B2 * | 12/2019 | Reddy | A61M 16/0463 | |
| 11,052,208 | B2 | 7/2021 | Curran et al. | | |
| 11,400,248 | B2 * | 8/2022 | Reddy | A61B 1/273 | |
| 2002/0045796 | A1 | 4/2002 | O'Connor et al. | | |
| 2003/0024533 | A1 * | 2/2003 | Sniadach | A61M 16/06 | 128/206.28 |
| 2003/0230678 | A1 * | 12/2003 | Bellmore | F16L 3/237 | 248/74.1 |
| 2004/0188571 | A1 * | 9/2004 | Stigler | B60R 16/0215 | 248/74.1 |
| 2009/0020128 | A1 | 1/2009 | Metzger et al. | | |
| 2009/0084385 | A1 * | 4/2009 | Lang | A61M 16/0463 | 128/207.11 |
| 2010/0025272 | A1 * | 2/2010 | Stau | F16L 55/035 | 206/349 |
| 2010/0122704 | A1 * | 5/2010 | Moenning, Jr. | A61M 16/06 | 128/206.28 |
| 2010/0122705 | A1 * | 5/2010 | Moenning, Jr. | A61M 16/104 | 128/206.24 |
| 2010/0122706 | A1 * | 5/2010 | Moenning, Jr. | A61M 16/06 | 128/206.28 |
| 2012/0009012 | A1 * | 1/2012 | Allenbach | F16L 3/2235 | 403/344 |
| 2013/0064734 | A1 * | 3/2013 | Allen | A61B 50/20 | 248/346.04 |

(56) References Cited

U.S. PATENT DOCUMENTS

| | | | | |
|---|---|---|---|---|
| 2014/0246024 | A1* | 9/2014 | Cragg | A61M 16/0833 128/204.19 |
| 2014/0246025 | A1* | 9/2014 | Cragg | A61M 16/0866 128/204.19 |
| 2014/0366890 | A1* | 12/2014 | Tao | A61M 16/009 128/849 |
| 2015/0202473 | A1 | 7/2015 | Curran et al. | |
| 2016/0053918 | A1* | 2/2016 | Flynn | F16L 3/237 248/68.1 |
| 2016/0074268 | A1 | 3/2016 | Breegi | |
| 2016/0286992 | A1* | 10/2016 | Sladics | A47G 19/2222 |
| 2017/0209656 | A1* | 7/2017 | Linton | A61M 16/0605 |
| 2017/0219127 | A1* | 8/2017 | Vermillion | F16B 2/22 |
| 2017/0259018 | A1* | 9/2017 | Blasdell | A61M 16/009 |
| 2017/0361057 | A1* | 12/2017 | Blasdell | A61M 16/009 |
| 2018/0133429 | A1* | 5/2018 | Reddy | A61M 16/024 |
| 2018/0344490 | A1* | 12/2018 | Fox | B23P 19/02 |
| 2019/0091434 | A1* | 3/2019 | Reddy | A61M 39/02 |
| 2020/0038617 | A1 | 2/2020 | Varga et al. | |
| 2021/0307872 | A1 | 10/2021 | Vizulis et al. | |
| 2021/0346624 | A1* | 11/2021 | Fiorenza | A61M 16/009 |

FOREIGN PATENT DOCUMENTS

| | | | | | |
|---|---|---|---|---|---|
| GB | 2367757 | A * | 4/2002 | A62B 9/003 |
| WO | WO-2012146369 | A2 * | 11/2012 | A61M 16/0078 |
| WO | WO2021207292 | | 10/2021 | |

OTHER PUBLICATIONS

Sovereign Medical, Inc.; Exhlo Shield; Product Information Sheet; Online; Apr. 3, 2020; entire document; https://sovmed.com/wp-content/uploads/2020/07/EXHALO-Introduction-Summary-Soverign-Medical-ed3.pdf.

International Search Report and Written Opinion for PCT/US2021/048141; United States Patent Office; Nov. 17, 2021; entire document.

* cited by examiner

VACUUM SHIELD ASSEMBLY FOR ATTACHMENT TO MEDICAL MASKS

FIELD OF INVENTION

The present invention relates to attachments to masks for medical procedures.

BACKGROUND

Medical masks may be used for or for nebulizing a patient or used for Non-Invasive Positive Pressure Ventilation (NIPPV), Bi-level Positive Airway Pressure (BIPAP), Bag-Valve-Mask Resuscitator (BVM), Demand-Valve Resuscitator (DVR), or Constant Positive Airway Pressure (CPAP). Of the masks that currently exist, none are believed to provide a truly efficient means for vacuuming air to create negative pressure, or for implementing a nebulizing or positive pressure procedure and at the same time using negative pressure to vacuum exhaled air from the patient. Accordingly, the industry would benefit by providing a vacuum shield assembly for attachment to a medical mask that may be used for vacuuming exhaled air from patient during nebulization, BIPAP or CPAP. Such a vacuum shield assembly would provide the added benefit of at least partially reducing contact to the mask and/or face of the patient, which may help to counter the risk of contagion of airborne illnesses, e.g., influenza, covid-19, etc., providing added protection to medical providers and staff involved in these procedures and in at least partially reducing the development of fomites from exhaled or aerosolized particles or droplets. Additionally, a benefit in the industry would be provided if such a vacuum shield assembly would be disposable as it would further reduce such risk of contagion. An even further benefit would be provided if such a vacuum shield assembly would be sufficiently versatile to be used as a primary and/or a secondary air vacuuming component, and/or a nebulizing component. Yet a further benefit would be realized if this vacuum shield assembly would be provided in different shapes and sizes to correspond to the geometry and size of the underlying face mask.

SUMMARY

The present invention is directed to a vacuum shield assembly intended for attachment to an existing mask. As used herein, an "existing mask" refers to a suction mask, a mask configured for attachment to a nebulizer, BIPAP, CPAP, BVM, DVR or another related mask, that is already disposed on the head and/or face of a patient. Accordingly, the vacuum shield assembly of the present invention may serve as a primary and/or a secondary suction or vacuum mechanism, which in some embodiments may be connected to a negative pressure vacuum. The vacuum shield assembly generally comprises a shield body and a retaining assembly. The retaining assembly may be used to connect the vacuum shield to a vacuum tube connected to a negative pressure vacuum. The retaining assembly may also be attached to a nebulizer unit or component thereof, or to the oxygen supply tube of a BIPAP or CPAP mask. Additionally, the shield body may comprise a lower segment. The shield body may be configured with or without a circular access opening in the convexity of the shield body that will allow a BVM, or DVR to connect to an existing mask by way of the access opening in order to facilitate the vacuuming of exhaled air during said procedures. The lower segment may further define an interior or inside of the shield body and may comprise a connecting portion disposed in fluid communication with the retaining assembly and the vacuum tube. The shield body may be configured and dimensioned to correspond to the geometry of the existing mask. As an example, the shield body may comprise a substantially concave configuration and/or a variety of shapes, including, but not limited to, a substantially triangular or substantially ovoidal shape. However, other shapes of the shield body are possible, which may also to correspond to the shape of the existing mask and/or the shape of the face and/or head of the patient. As such, it is within the scope of the present invention that the vacuum shield assembly according to the present invention at least partially remove exhaled infectious particles, for example, from a patient that has a respiratory illness. As a result, it is contemplated that such increased removal of exhaled infectious particles at least partially reduce the risk of contagion of medical practitioners and staff assisting with these types of procedures and/or the contamination of physical objects in the vicinity (fomites).

BRIEF DESCRIPTION OF THE DRAWINGS

FIG. 15B FIG. 15A is a perspective view of another embodiment of a shield body of the vacuum shield assembly according to the present invention comprising a vacuum attachment disposed on the shield body and connected to a BVM or DVR unit.

DETAILED DESCRIPTION

Figure 1:
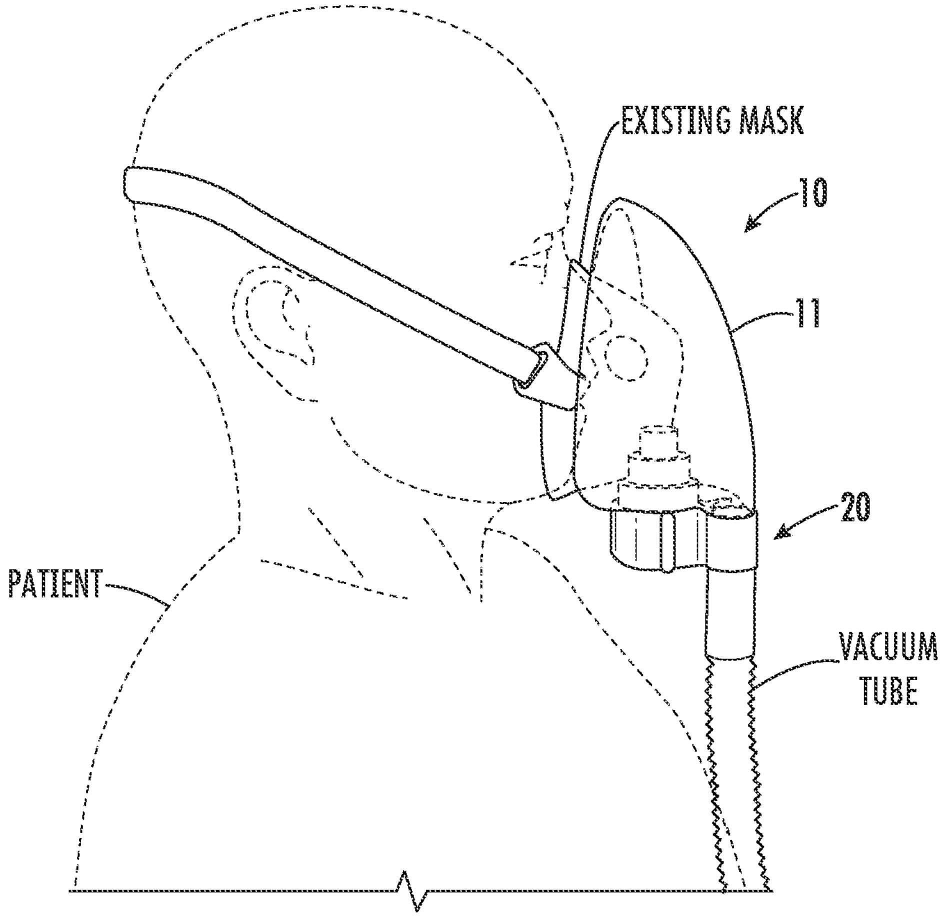
FIG. 1 is a perspective view of one embodiment of the vacuum shield assembly according to the present invention attached to nebulizer mask.
Figure 2:
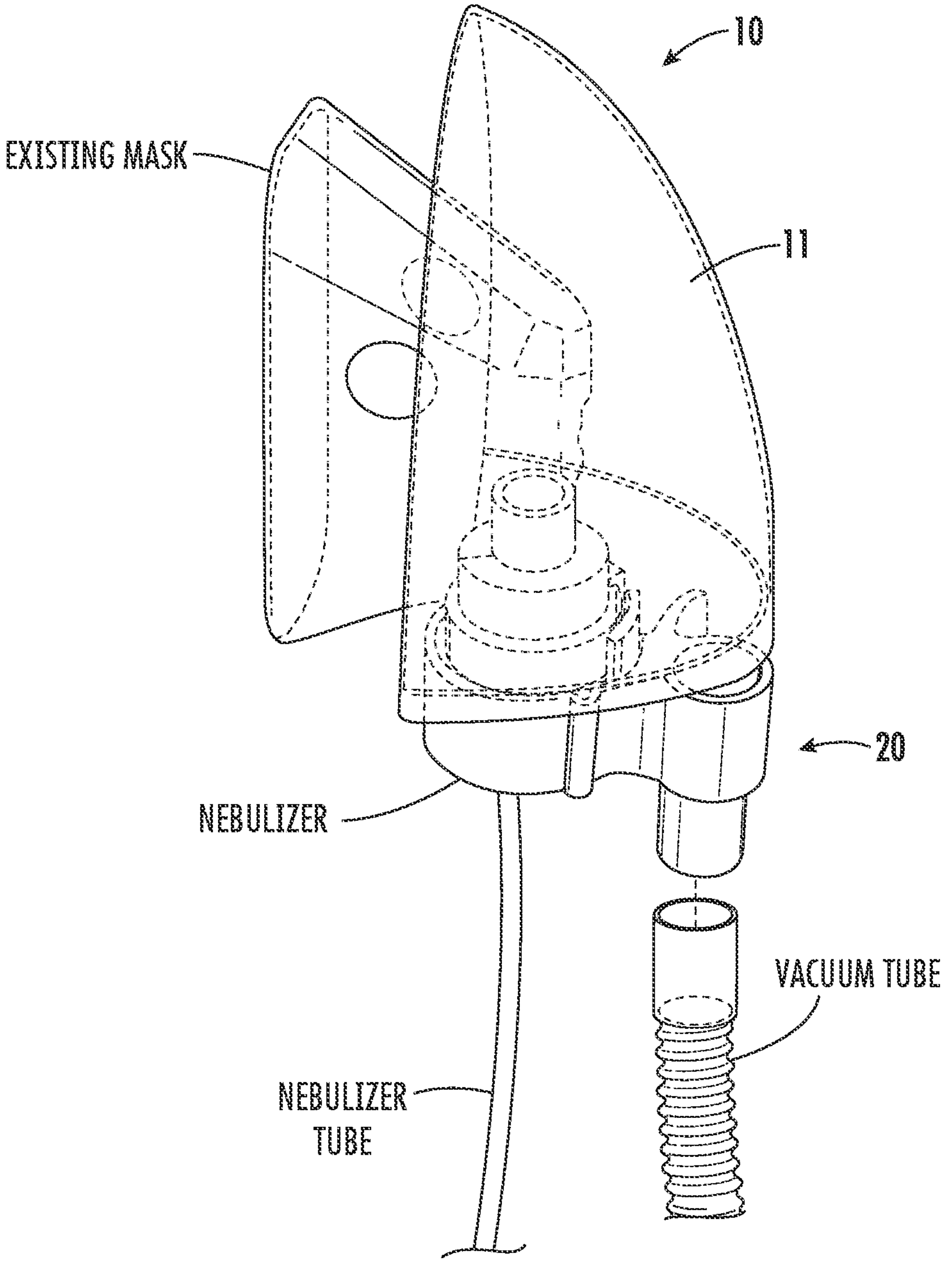
FIG. 2 is a perspective view of another embodiment of the vacuum shield assembly according to the present invention for use with a nebulizer mask.
Figure 3:
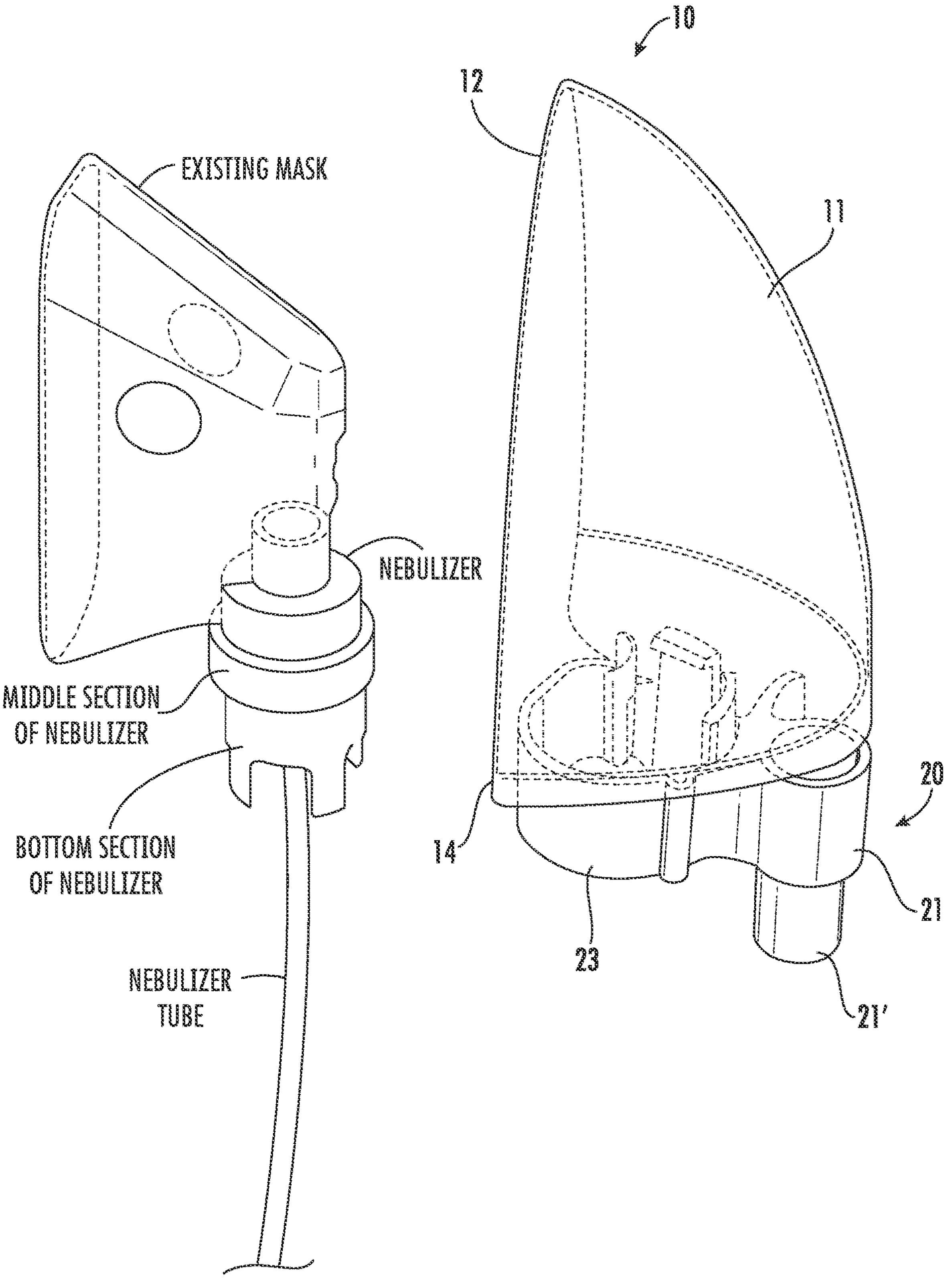
FIG. 3 is a perspective view of yet another embodiment of the vacuum shield assembly according to the present invention for use with a nebulizer mask.
Figure 4:
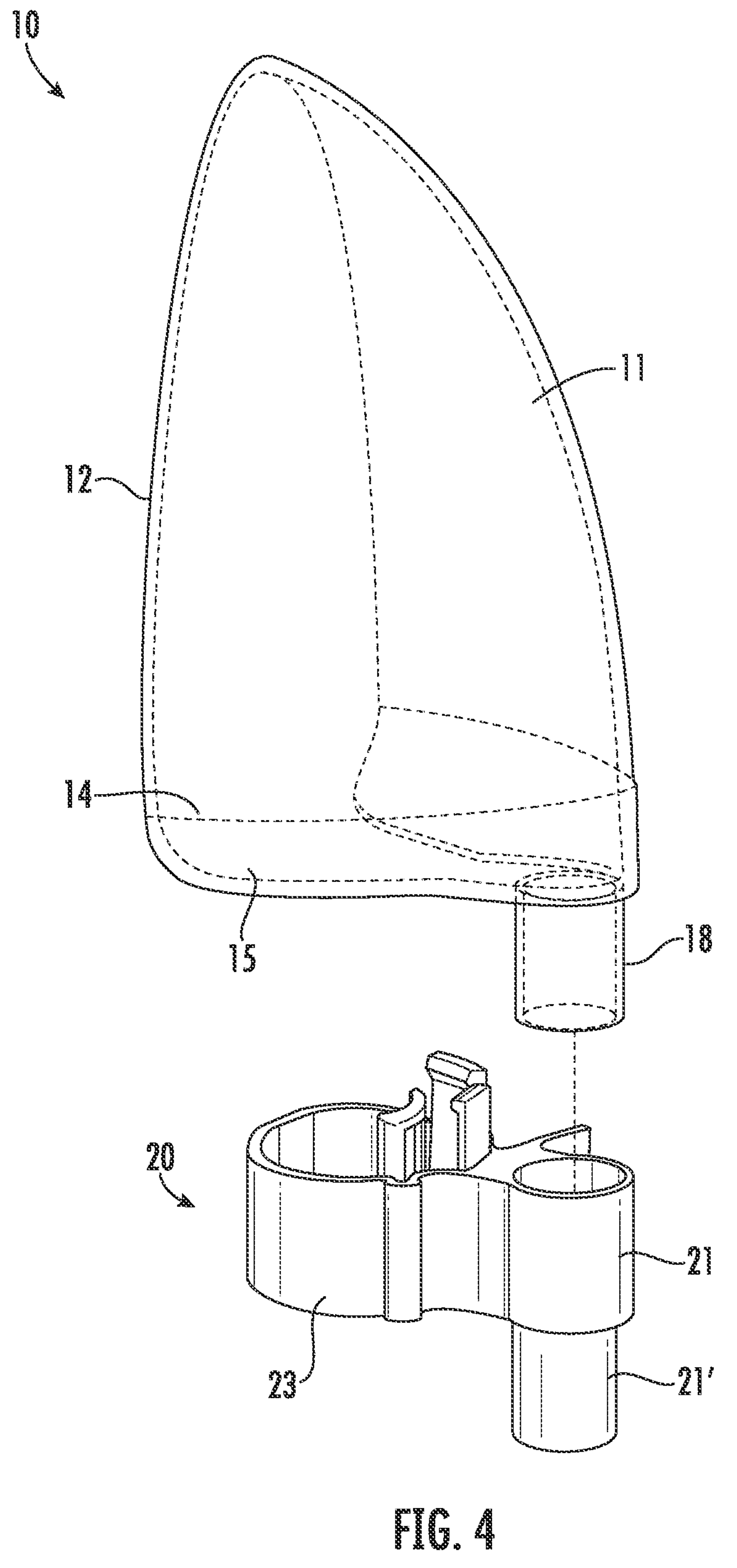
FIG. 4 is a perspective and partially exploded view of a further embodiment of the vacuum shield assembly according to the present invention.
Figure 6:
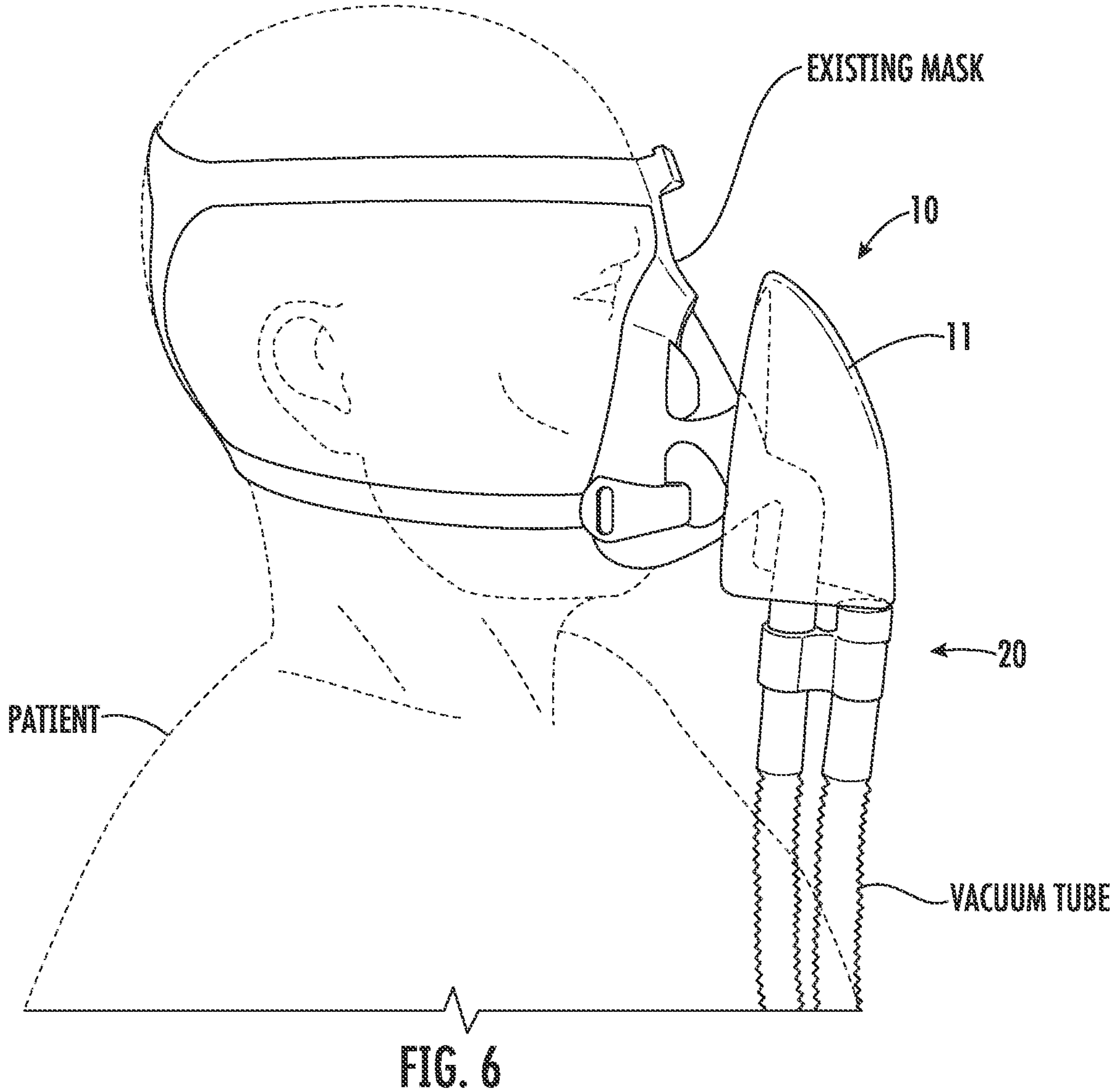
FIG. 6 is a perspective view of one embodiment of the vacuum shield assembly according to the present invention attached to a BIPAP or CPAP mask.
Figure 7:
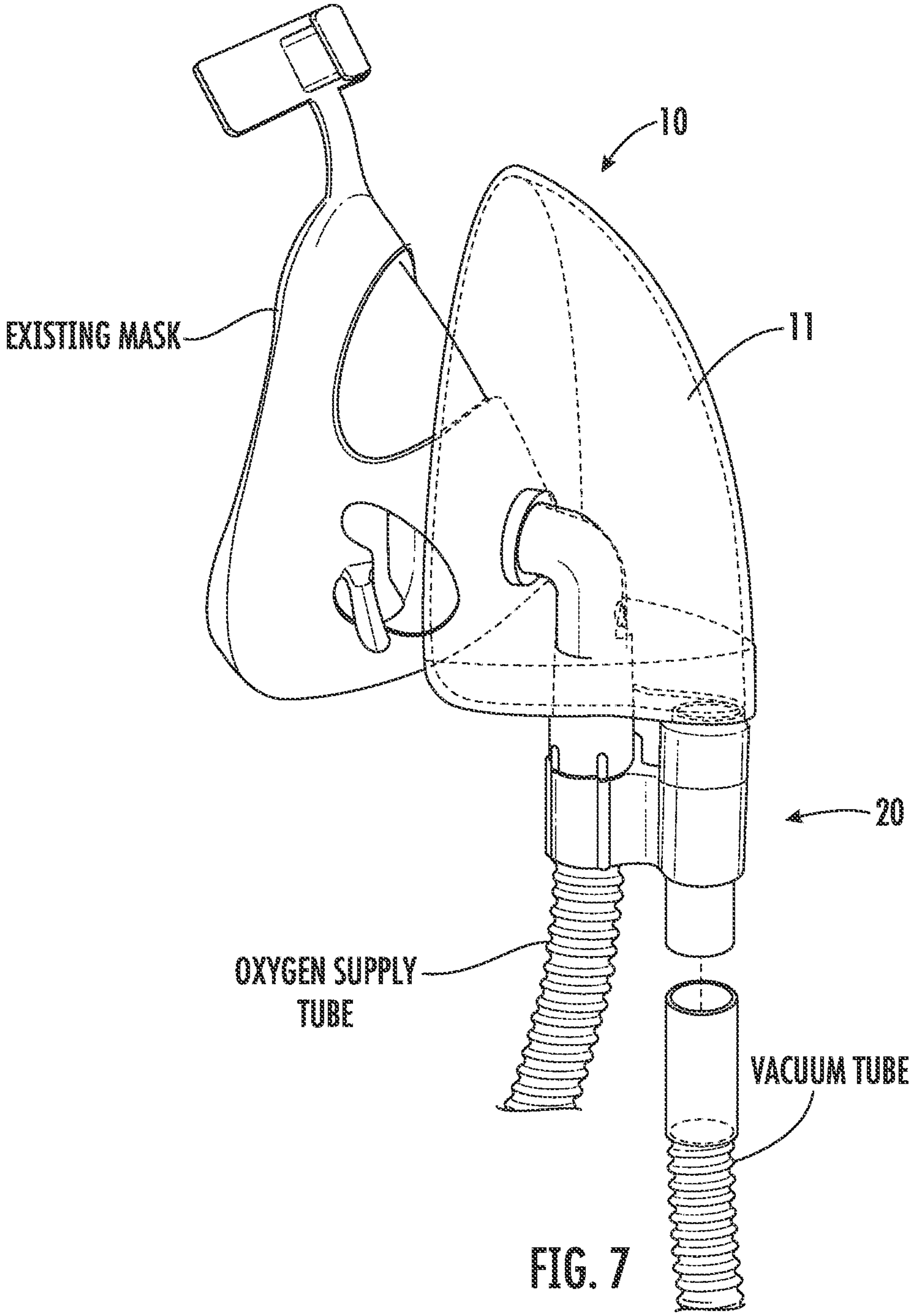
FIG. 7 is a perspective view of another embodiment of the vacuum shield assembly according to the present invention for use with a BIPAP or CPAP mask.
Figure 8:
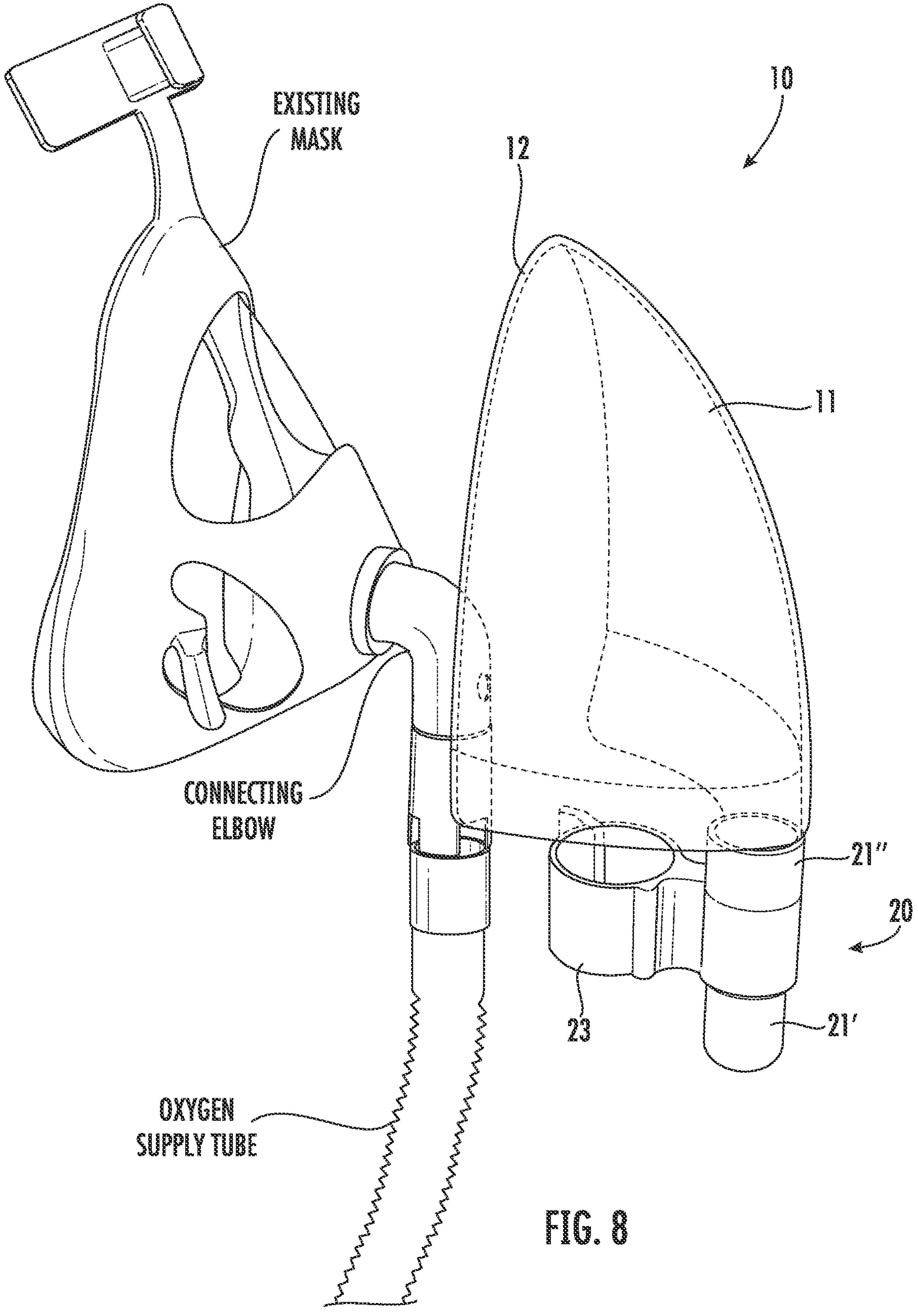
FIG. 8 is a perspective view of yet another embodiment of the vacuum shield assembly according to the present invention for use with a BIPAP or CPAP mask.
Figure 9:
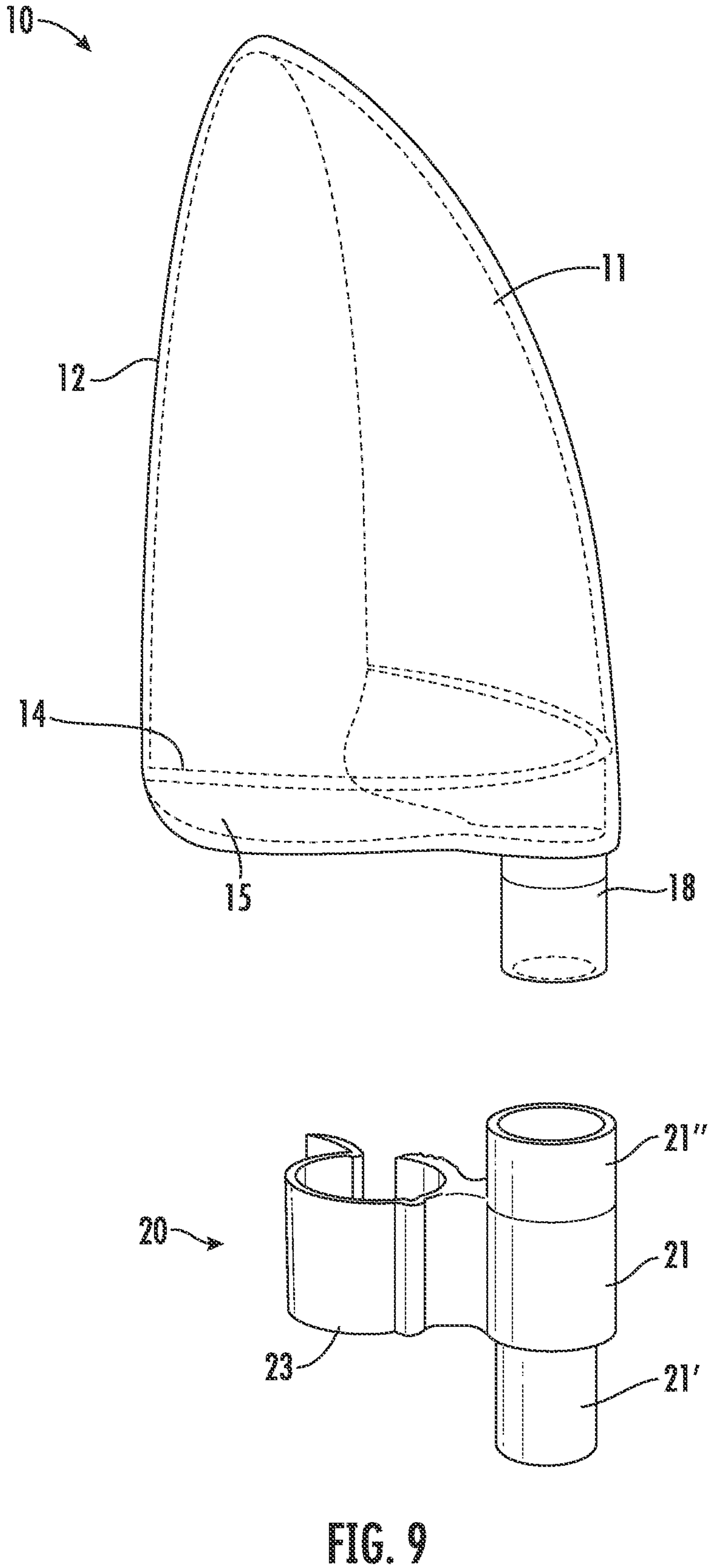
FIG. 9 is a perspective and partially exploded view of an even further embodiment of the vacuum shield assembly according to the present invention.
Figure 10:
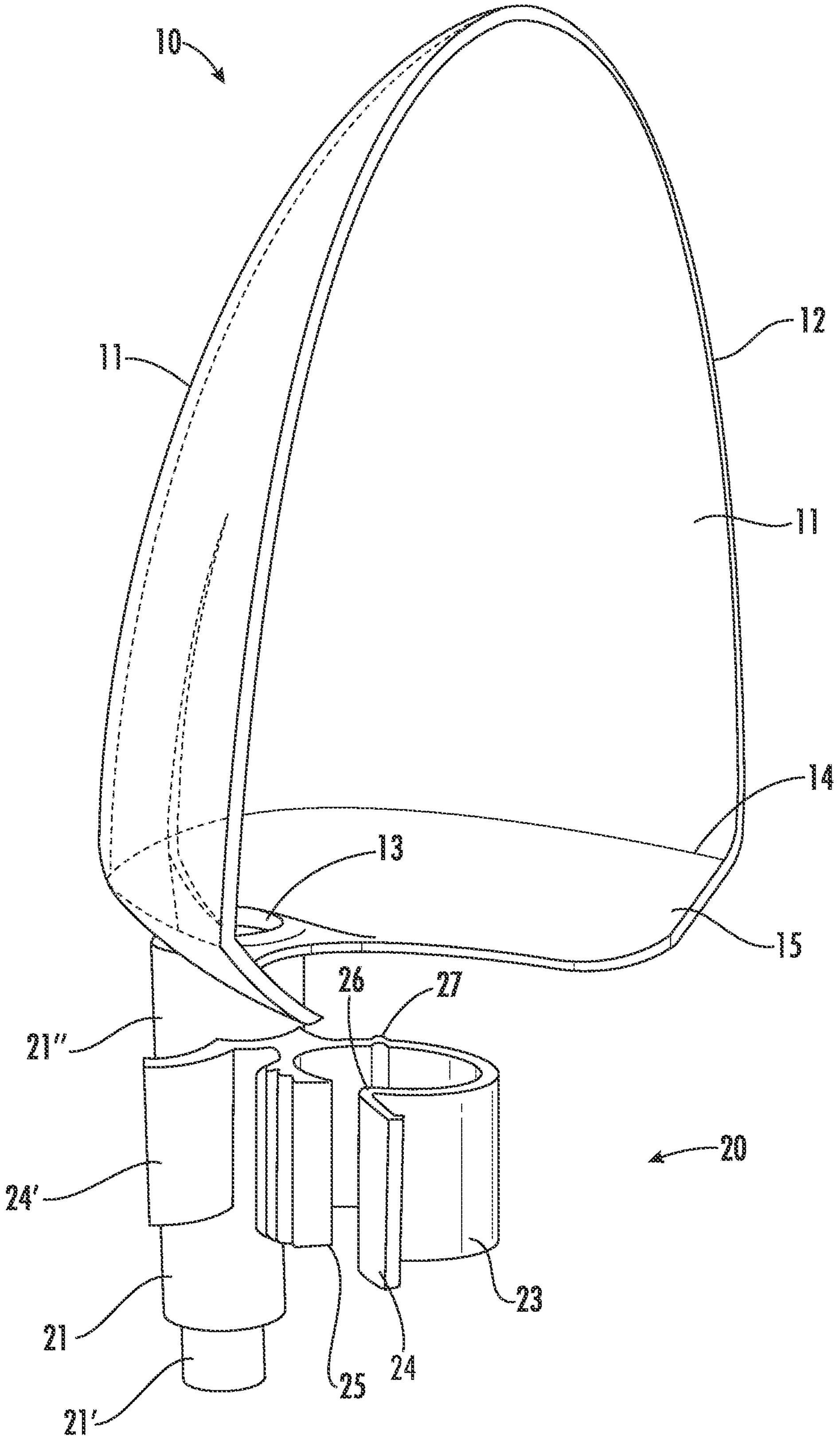
FIG. 10 is a perspective view of yet a further embodiment of the vacuum shield assembly according to the present invention.

With initial reference to FIGS. 1-4, 6-10 and 12, the present invention is directed to a vacuum shield assembly 10. The vacuum shield assembly 10 according to the present invention is intended to be disposed on the head and/or face of a patient that is already wearing a medical mask, and is intended to at least partially extract exhaled air from the patient. For example, and as is perhaps best shown in FIGS. 1 and 6, the vacuum shield assembly 10 may be attached to a mask already disposed on the head and/or face of a patient. The vacuum shield assembly 10 may be connected to a vacuum tube such that it may at least partially extract exhaled air from the patient, including, for example, between the already disposed medical mask and the inside of a shield body 11 of the vacuum shield assembly 10. The vacuum shield assembly 10 may serve as a primary suction or vacuum mechanism, or alternatively, as secondary suction or vacuum mechanism. As an example, and as is shown in FIGS. 6-8, the vacuum shield assembly 10 may be attached to a BIPAP or CPAP mask already disposed on the head and/or face of a patient. As a further example, and as is shown in FIGS. 1-3, the vacuum shield assembly 10 may be attached to a nebulizing mask already disposed on the head and/or face of a patient.

As shown at least in the illustrative embodiments of FIGS. 1-4, 6-10 and 12, the vacuum shield assembly 10 comprises a shield body 11. The vacuum shield assembly 10 also generally comprises a retaining assembly 20. The retaining assembly 20 is generally connected to the shield body 11 as well as to a vacuum tube. As used herein, the term "vacuum tube" refers to a conduit, hose, or other related structure that may convey air from a patient and/or mask to another location, and which may be connected to a negative pressure vacuum. As shown at least in FIGS. 2 and 7, the retaining assembly 20 may be used to interconnect the shield body 11 to a vacuum tube. The structure of the retaining assembly 20 should define a fluid communication between an inside of the shield body 11 and the vacuum tube. As such, the shield body 11 may create a negative pressure on an interior thereof to remove the air between the medical mask, the face and/or head of the patient, and the interior or inside of the shield body 11. It is contemplated that a patient that is wearing a BIPAP or CPAP mask, or a nebulizing mask, be able to exhale through the mask, and that at least a portion of this exhaled air may be captured by the negative pressure generated by the shield body 11 and the vacuum tube.

As is shown in FIGS. 1-2 and 6-7 the retaining assembly 20 may also be used to connect the shield body 11 and/or vacuum tube to an oxygen supply tube and/or a nebulizing unit or component thereof. Shield bodies of different sizes may be attached to a retaining assembly 20, for example, by inserting a connecting portion 18 into an upper section 21" of the retaining component 21, or to the retaining component 21 directly, which will be explained later. As such, it may be possible to switch between shield bodies of different sizes according to a specific need, e.g., air suction, nebulization, etc., and/or geometrical constraints, e.g., the size of the head of the patient.

Figure 12:
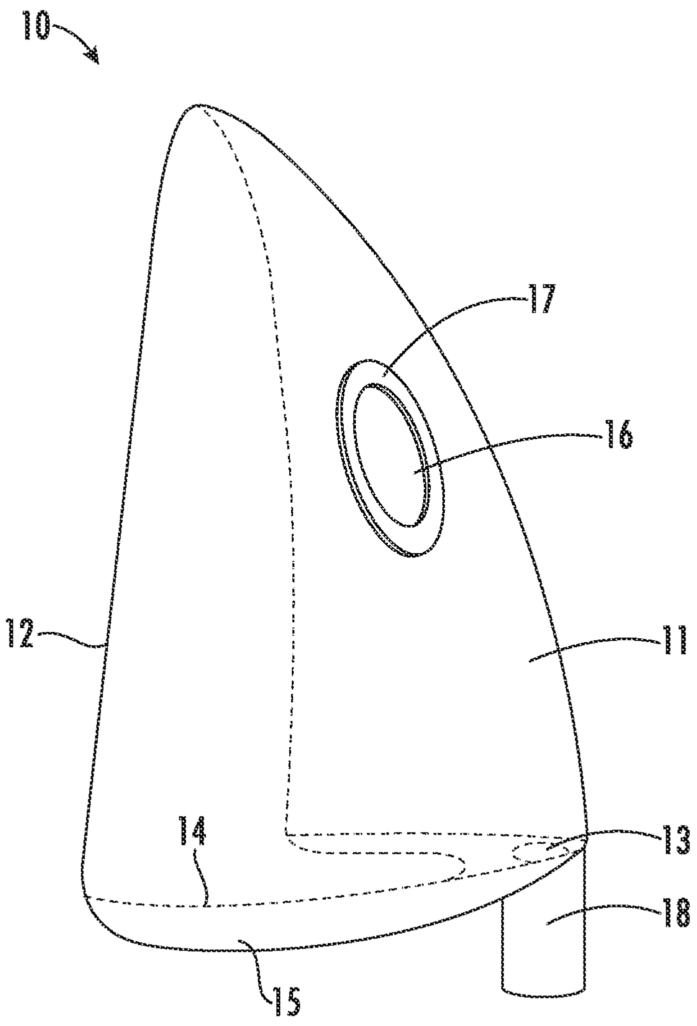
FIG. 12 is a perspective view of one embodiment of a shield body of the vacuum shield assembly according to the present invention comprising a second opening.
Figure 12A:
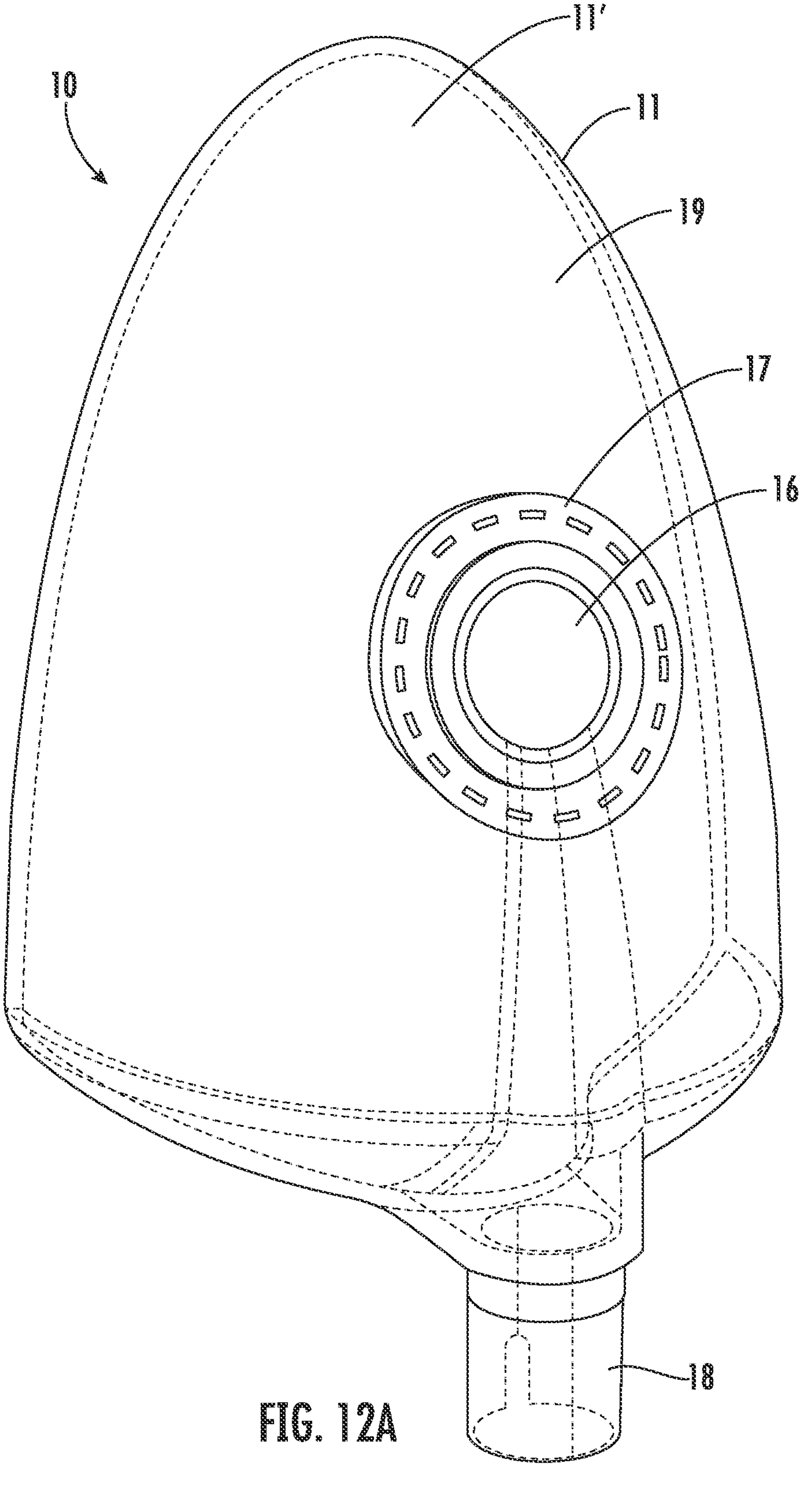
FIG. 12A is a perspective view of another embodiment of a shield body of the vacuum shield assembly according to the present invention comprising a second opening.
Figure 12B:
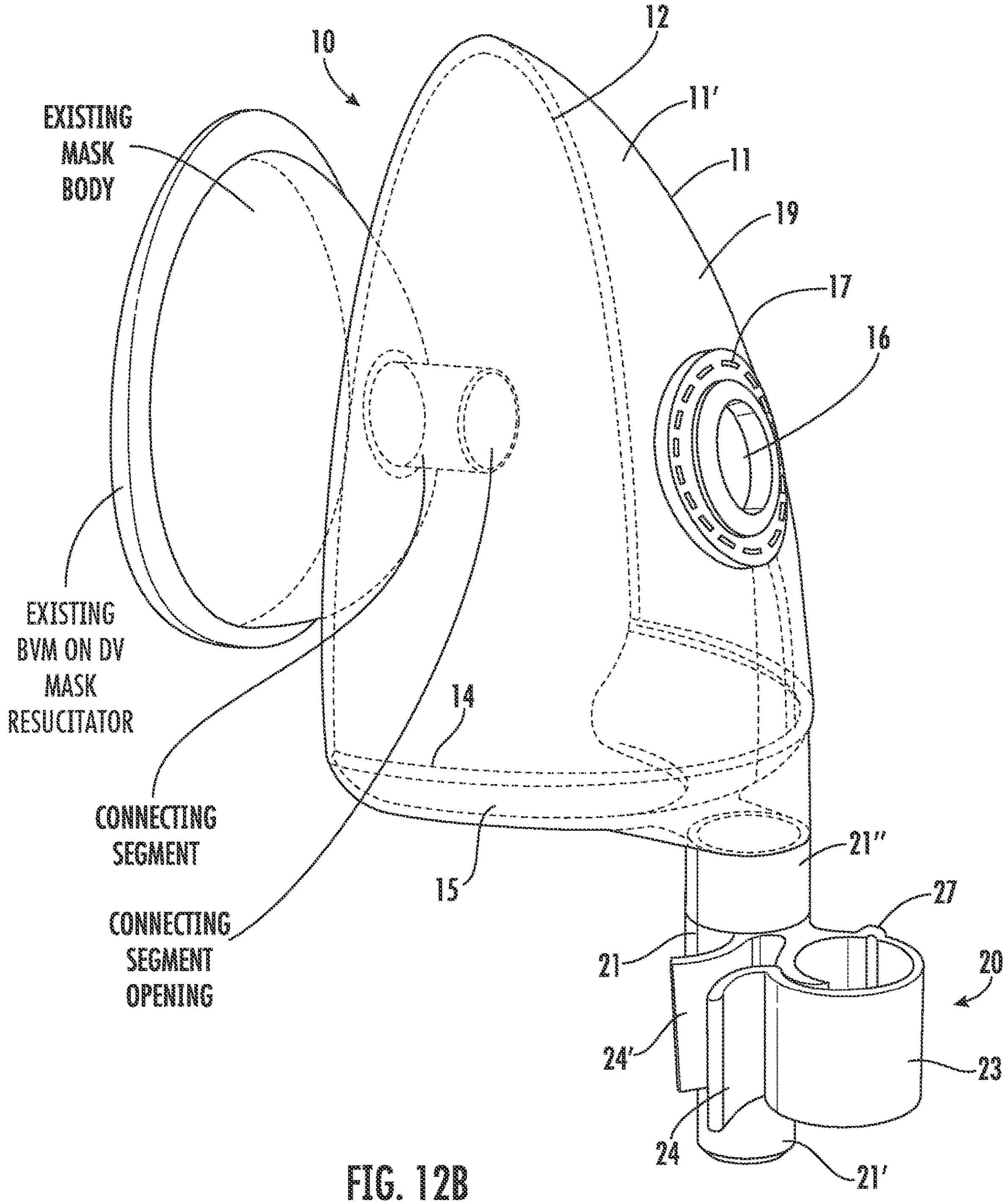
FIG. 12B is a perspective view of yet another embodiment of a shield body of the vacuum shield assembly according to the present invention comprising a second opening.
Figure 12C:
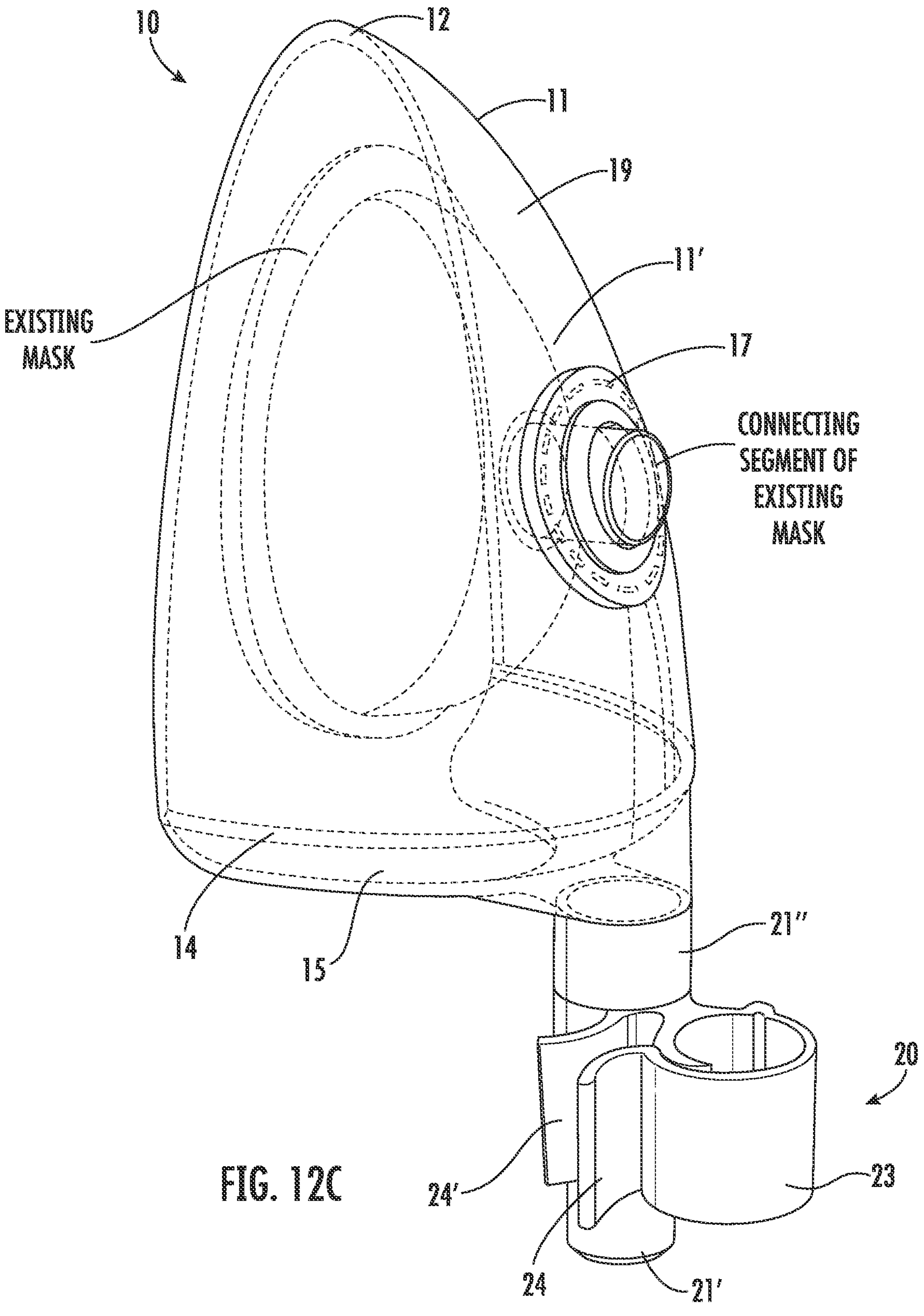
FIG. 12C is a perspective view of even another embodiment of a shield body of the vacuum shield assembly according to the present invention comprising a second opening.
Figure 12D:
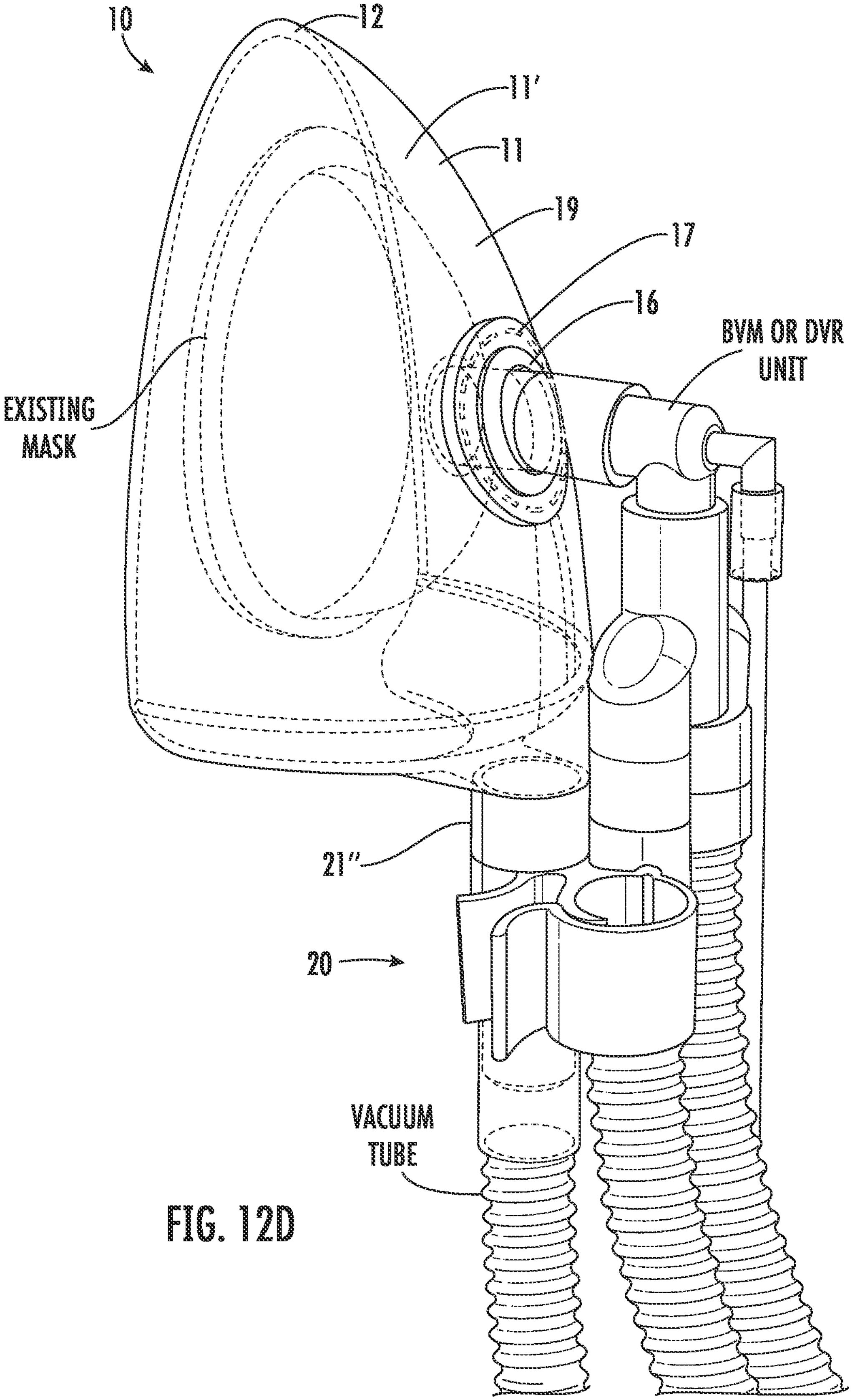
FIG. 12D is a perspective view of an even further embodiment of a shield body of the vacuum shield assembly according to the present invention comprising a second opening and connected to a BVM or DVR unit.
Figure 13A:
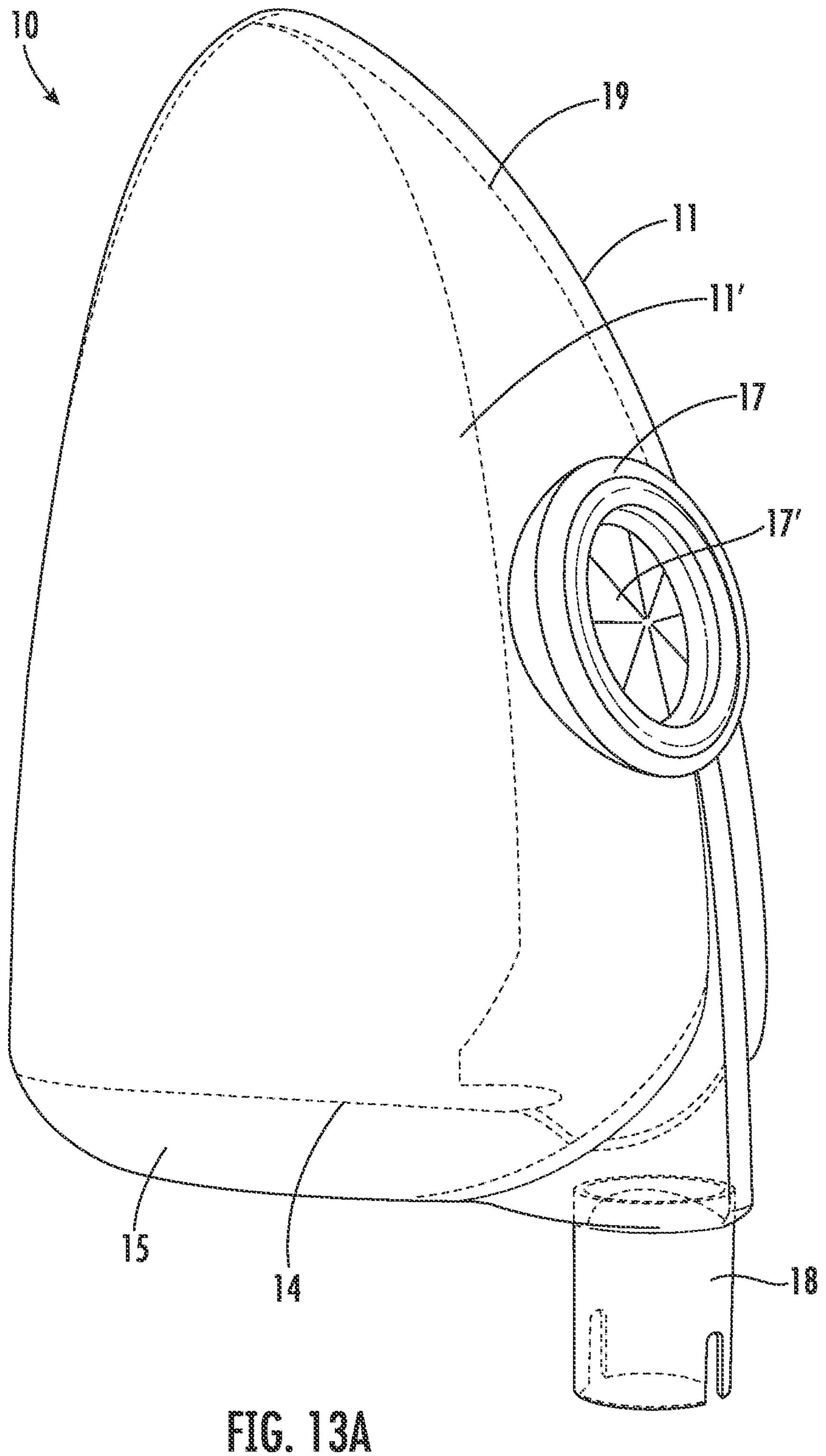
FIG. 13A is a perspective view of one embodiment of a shield body of the vacuum shield assembly according to the present invention comprising a vacuum attachment disposed on the shield body.
Figure 13B:
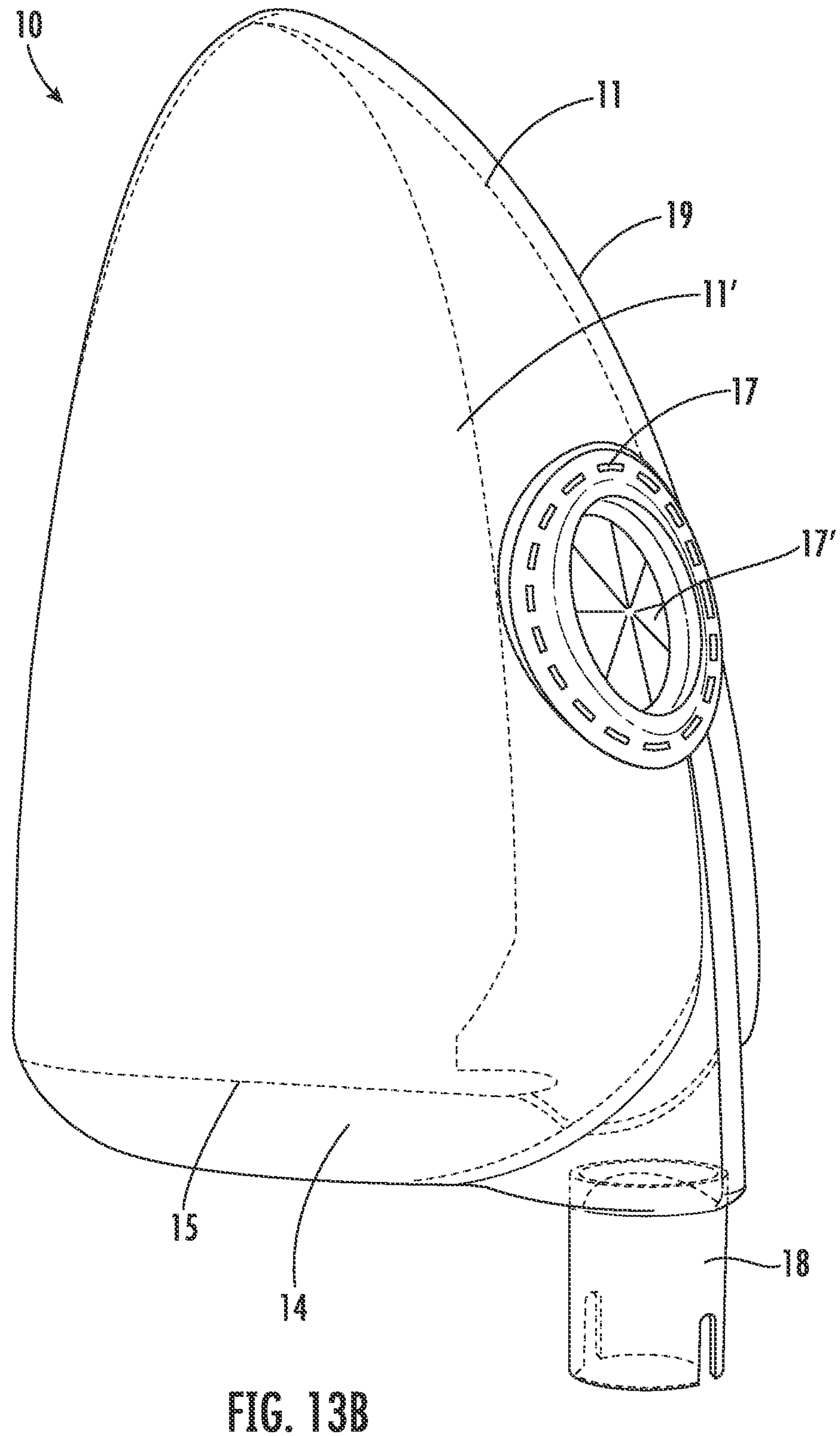
FIG. 13B is a perspective view of another embodiment of a shield body of the vacuum shield assembly according to the present invention comprising a vacuum attachment disposed on the shield body.
Figure 14A:
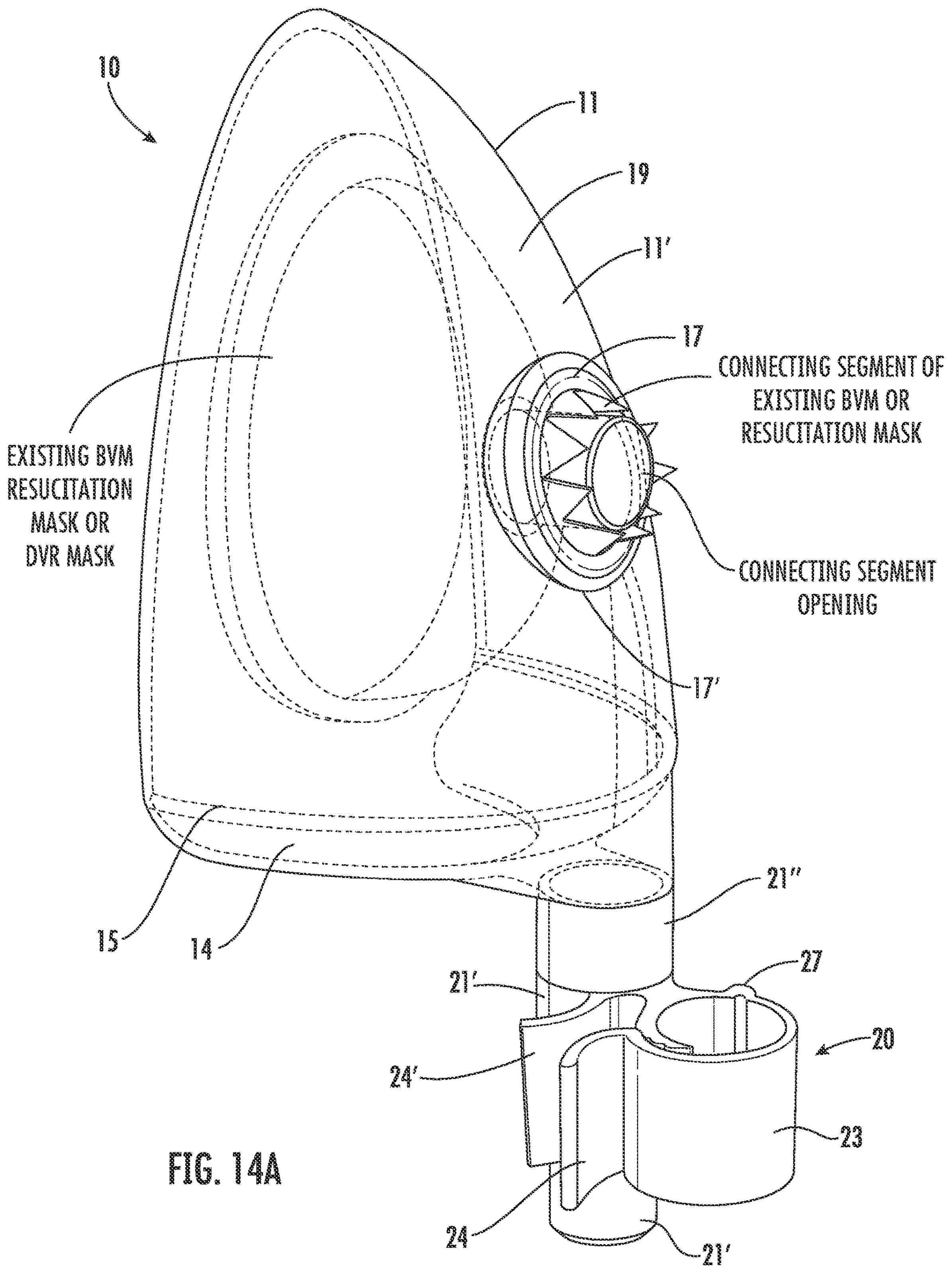
FIG. 14A is a perspective view of yet another embodiment of a shield body of the vacuum shield assembly according to the present invention comprising a vacuum attachment disposed on the shield body.
Figure 14B:
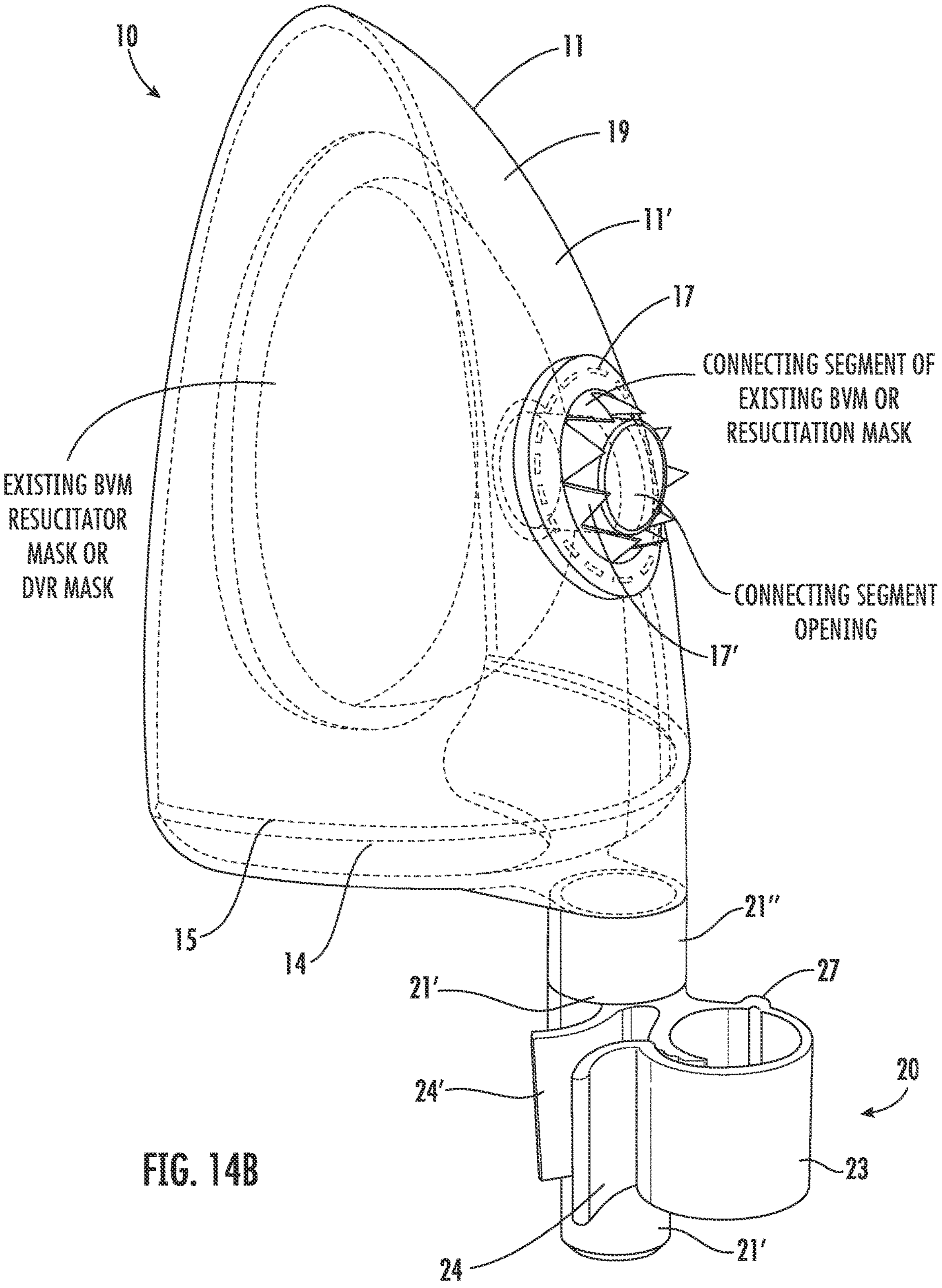
FIG. 14B is a perspective view of an even further embodiment of a shield body of the vacuum shield assembly according to the present invention comprising a vacuum attachment disposed on the shield body.
Figure 15A:
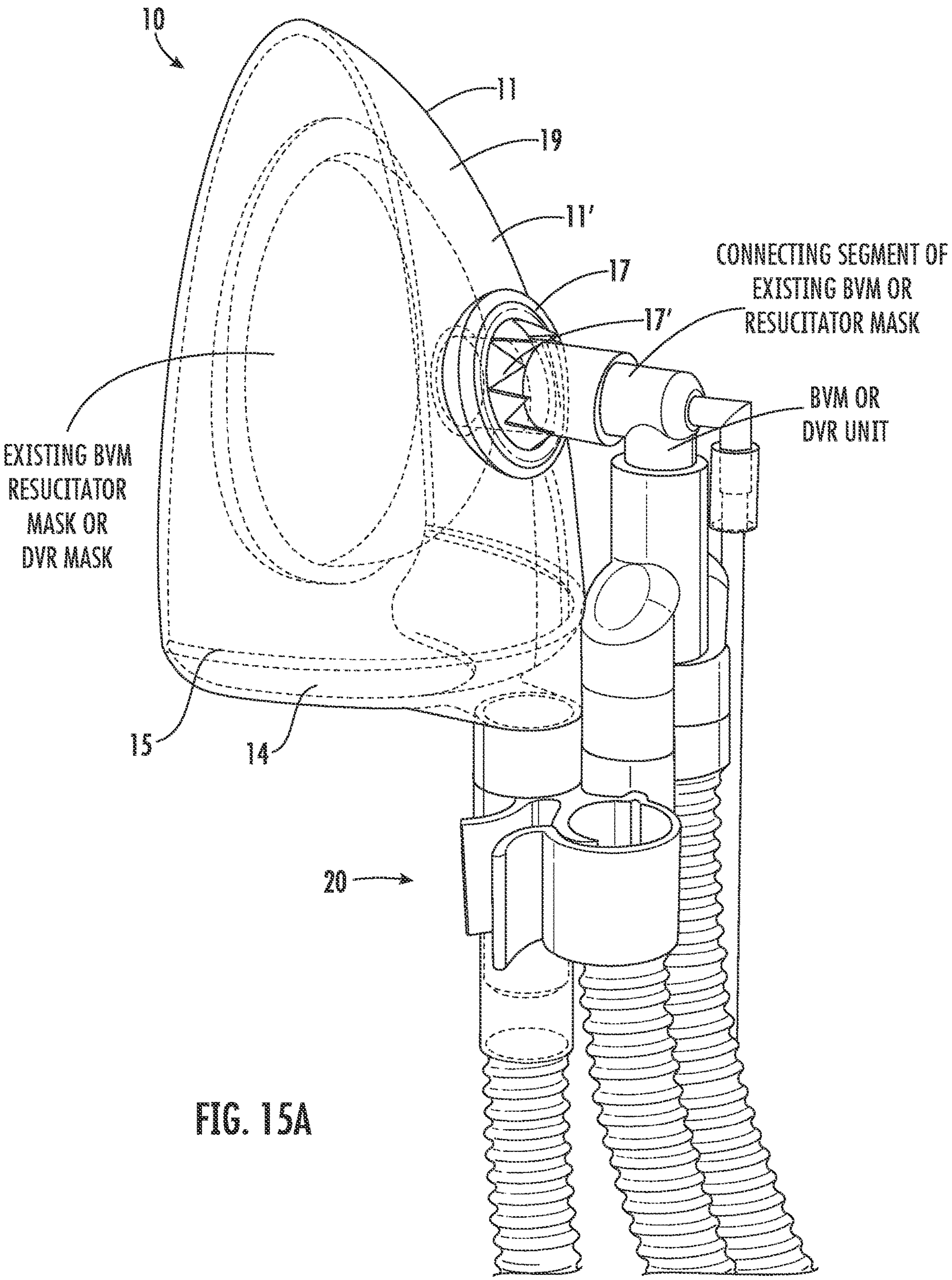
FIG. 15A is a perspective view of one embodiment of a shield body of the vacuum shield assembly according to the present invention comprising a vacuum attachment disposed on the shield body and connected to a BVM or DVR unit.
Figure 15B:
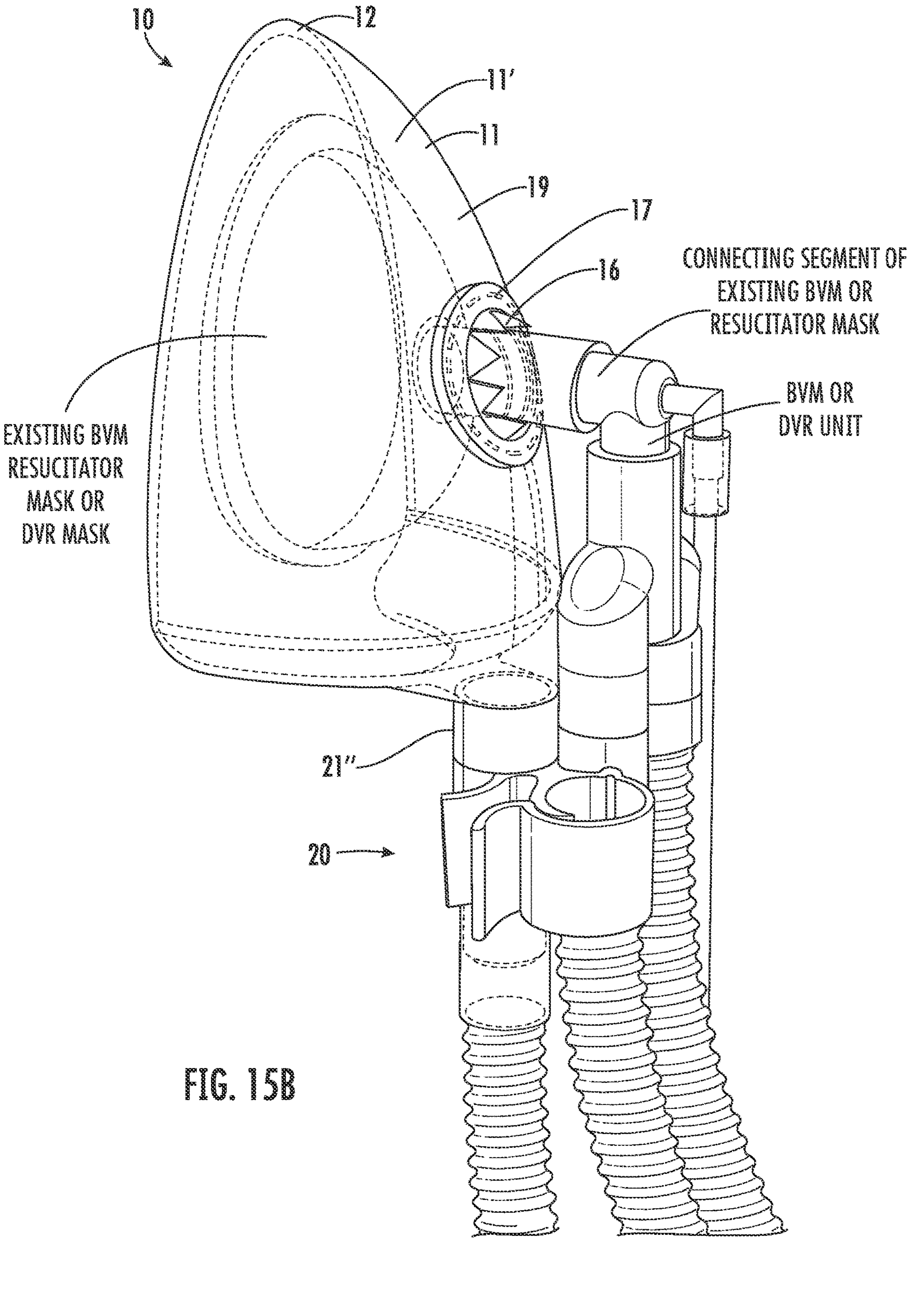

With reference to FIGS. 12A-15B, the shield body 11 according to the inventive vacuum shield assembly 10 may be provided with a second opening 16 configured and dimensioned to accommodate a medical mask. With specific reference to FIGS. 12B-12D and 14A-15B, the second opening 16 may be configured and dimensioned so that a connecting segment of an existing medical mask, e.g., a demand-valve resuscitator (DVR) mask or a bag-valve-mask (BVM) resuscitator mask, may be inserted there through, e.g., as shown in FIGS. 12D, 15A and 15B. Furthermore, the shield body 11 may be provided with a vacuum attachment 17, which may at least partially define or otherwise form a seal between an outer surface 11' and an inner surface 11" of the shield body 11. Also, the second opening 16 and/or vacuum attachment 17 may be operatively configured and dimensioned to substantially define a seal between the second opening 16 and the connecting segment of the medical mask. Accordingly, the vacuum attachment 17 may comprise a grommet component or grommet seal. However, this is not necessarily limiting as other configurations of the vacuum attachment 17 are also possible.

As represented in at least FIG. 15A, a grommet seal may be co-molded to the shield body 11. This is advantageous as it may at least partially reduce the time, effort, and/or expense involved in manufacturing a vacuum shield assembly 10 with a vacuum attachment. Further, a grommet seal co-molded to the shield body may provide for a robust construction, which is also advantageous. Alternatively, as represented at least in FIG. 15B, a grommet seal may be inserted into the shield body, which is referred to as an insert-molding. Alternatively, the Further, the vacuum attachment 17 may comprise a variety of materials, including, but not necessarily limited to silicone, rubber, plastics, elastomeric polymers, seals, sealants, and/or other related structures. As such, the second opening 16 may at least partially allow an operative communication between the existing mask, i.e., BVM or DVR, through an interior of its connecting segment, and the underlying BVM or DVR unit. It is contemplated that the opening 16 permit at least a fluid communication between the existing mask and the BVM or DVR unit, i.e., via the interior of the connecting segment of the mask, which passes through the second opening 16. With reference again to FIGS. 12A-15B, the second opening 16 may be disposed on the shield body 11 at a location that corresponds to the location of the medical mask. Generally, during some BVM and/or DVR procedures some air may leak between the face of the patient and the mask, which is attached to the patient, for example, as the patient inhales or exhales air. In such BVM and/or DVR procedures, the inventive vacuum shield assembly 10 is intended to capture exhaled air that may leak out of the BVM and/or DVR mask. As such, the second opening 16 may be disposed substantially around a middle section of the shield body 11 and/or above the first opening 13. This would allow for placement of the vacuum shield assembly 10 on a location that corresponds to location of the connecting segment of the medical mask. Moreover, the second opening 16 and/or vacuum attachment 17 may be disposed on a height along the shield body 11 that corresponds to the approximate location of the existing medical mask. As may be appreciated from the illustrative embodiments as shown in FIGS. 15A and 15B, exhaled air may exit through the existing mask, i.e. through opening 13 of the shield body 11. In addition to, or in lieu of this, exhaled air may also exit through a vacuum tube operatively connected to the existing mask and connecting segment, which passes through the second opening 16.

Figure 16A:
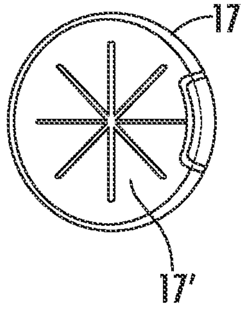
FIG. 16A is a top view of one embodiment of a vacuum attachment according to the vacuum shield assembly of the present invention.

As is perhaps best shown in FIGS. 16A-161, features of the present invention comprise providing a vacuum attachment 17 comprising a grommet configuration. As shown in FIGS. 16A-161, the vacuum attachment 17 may comprise a substantially circular shape configured to correspond to the diameter and/or size of the second opening 16. For example the diameter of an outer perimeter or recessed portion of the vacuum attachment 17 may be configured to correspond to the dimension and/or size of the second opening 16. Additionally, the circular shape of the vacuum attachment 17 may be configured and dimensioned to correspond to the diameter and/or size of the connecting segment of the medical mask, for example around an inner perimeter of the vacuum attachment 17. As shown in FIGS. 16F and 16I, a vacuum attachment 17 may be provided comprising a grommet configuration with an aperture. As such, when the vacuum attachment 17 is disposed around the second opening 16, the aperture of the vacuum attachment 17 permits a fluid communication between the outer surface 11' and inner surface 11" through the second opening 16. As shown in FIG. 16F, the vacuum attachment 17 may comprise a tear away recessed pocket. Conversely, as shown in the illustrative embodiments of FIGS. 16A-16E and 16G-16H, the vacuum attachment may comprise a grommet configuration that creates a cover around the interior perimeter of the vacuum attachment 17. The cover may comprise a plurality of adjacently disposed segments 17', which may be collectively structured to form a substantially flat surface in an inoperative disposition of the connecting segment of the medical mask, i.e., when the connecting segment is not inserted around the second opening 16. The plurality of adjacently disposed segments 17' may be collectively structured to bend at least in an opposite direction to the movement of the connecting segment of the medical mask.

As is shown in the illustrative embodiments of FIGS. 15A and 15B, once the connecting segment of the medical mask is inserted through the second opening 16, the plurality of adjacently disposed segments 17' may bend towards the outer surface 11' allowing the connecting segment to pass there through. Conversely, if the connecting segment is removed, the plurality of adjacently disposed segments 17' may return to their natural and/or initial position, forming once again the cover around the aperture of the vacuum attachment 17. As such, a vacuum shield assembly 10 according to the present invention may be used in connection with one BVM and/or DVR procedure, then later removed, and used in a subsequent BVM and/or DVR procedure. The vacuum shield assembly 10 may also be used in connection with a procedure that uses the second opening 16, i.e., a BVM and/or DVR procedure, and may later be used in a subsequent procedure that does not use the second opening 16, or vice versa. Or alternatively, a vacuum shield assembly 10 comprising a second opening 16 may also be used in connection with a procedure that does not need the second opening 16. Thus, a vacuum shield assembly 10 comprising a second opening 16 may be attached to a medical mask that is not a BVM or DVR mask. As such, the plurality of adjacently disposed segments 17' may naturally form a cover, which should essentially function as a seal between the outer surface 11' and inner surface 11". Said differently, the plurality of adjacently disposed segments 17', in their natural position, should at least partially reduce leakage of exhaled air from the inner surface 11" to the outer surface 11'. As such, exhaled air may be retained on an interior of the shield body 11 and removed via the connecting portion 18 and/or oxygen tube.

Figure 16B:
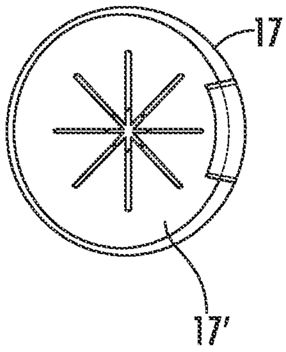
FIG. 16B is a top view of another embodiment of a vacuum attachment according to the vacuum shield assembly of the present invention.
Figure 16C:
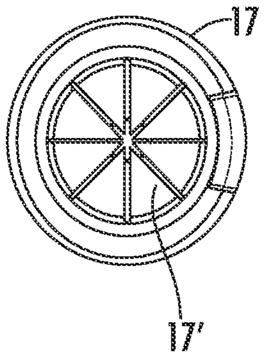
FIG. 16C is a top view of a further embodiment of a vacuum attachment according to the vacuum shield assembly of the present invention.
Figure 16D:
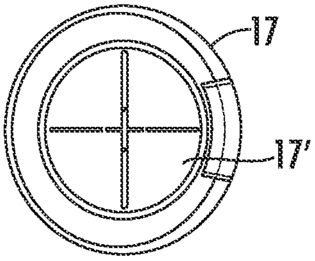
FIG. 16D is a top view of yet another embodiment of a vacuum attachment according to the vacuum shield assembly of the present invention.
Figure 16E:
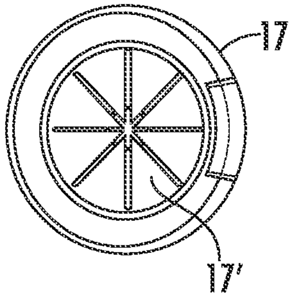
FIG. 16E is a top view of an even further embodiment of a vacuum attachment according to the vacuum shield assembly of the present invention.
Figure 16F:
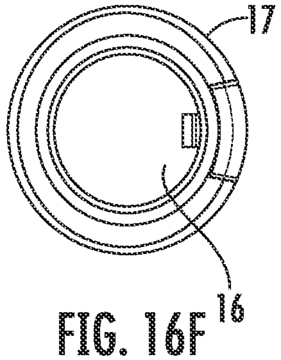
FIG. 16F is a top view of another embodiment of a vacuum attachment according to the vacuum shield assembly of the present invention.
Figure 16G:
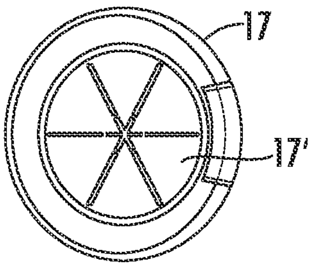
FIG. 16G is a top view of a further embodiment of a vacuum attachment according to the vacuum shield assembly of the present invention.
Figure 16H:
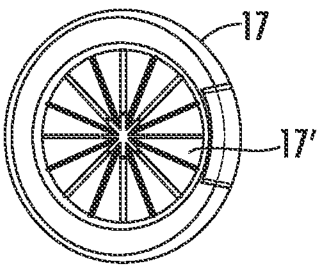
FIG. 16H is a top view of an even further embodiment of a vacuum attachment according to the vacuum shield assembly of the present invention.
Figure 16I:
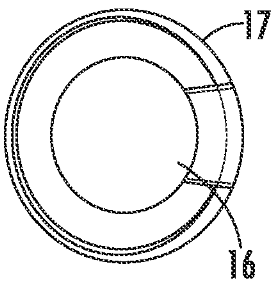
FIG. 16I is a top view of yet another embodiment of a vacuum attachment according to the vacuum shield assembly of the present invention.

As is also seen in FIGS. 16A-16E and 16G-16H, each one of the plurality of adjacently disposed segments 17' may comprise a substantially triangular shape. As such, when disposed around the inner perimeter of the vacuum attachment 17, they may substantially define a cover. By way of example, the plurality of adjacently disposed segments 17' comprising a substantially triangular shape may comprise four segments, e.g., FIG. 16D, six segments, e.g., FIG. 16G, eight segments, e.g., FIGS. 16A, 16B, 16C, 16E and 16H, or even more than eight segments. Furthermore, as shown in FIG. 16H, the plurality of adjacently disposed segments 17' may comprise reinforcement ribs. Also, the illustrative embodiments of FIGS. 16D-16E and 16G may comprise a top flush relief ring, or a recessed pocket as is shown in FIGS. 16C-16H. As shown in FIGS. 16A-16B, other possible configurations of the plurality of adjacently disposed segments comprises a top flush configuration without a relief ring.

As is perhaps best shown in FIGS. 5-6, and as mentioned below, the inventive vacuum shield assembly 10 comprises a retaining assembly 20. As shown in FIGS. 1 and 6, the retaining assembly 20 may be oriented towards the face of a patient, such that it may be used to attach the shield body 11 to an existing vacuum tube or other related component. Various connecting mechanism of the retaining assembly 20 may be implemented to connect it to the shield body 11, vacuum tube, oxygen supply tube or nebulizing unit. Said differently, the retaining assembly 20 may be used to interconnect the shield body 11 to the vacuum tube and the oxygen supply tube, an existing nebulizing unit and/or mask, or an existing BIPAP or CPAP mask. As an example, the retaining assembly 20 may comprise clamps or connecting arms. Other mechanisms of the retaining assembly 20 are also within the scope of the present invention and may comprise adhesives, connecting bands, snap-on mechanisms, magnets, or another related connecting mechanisms.

Figure 5:
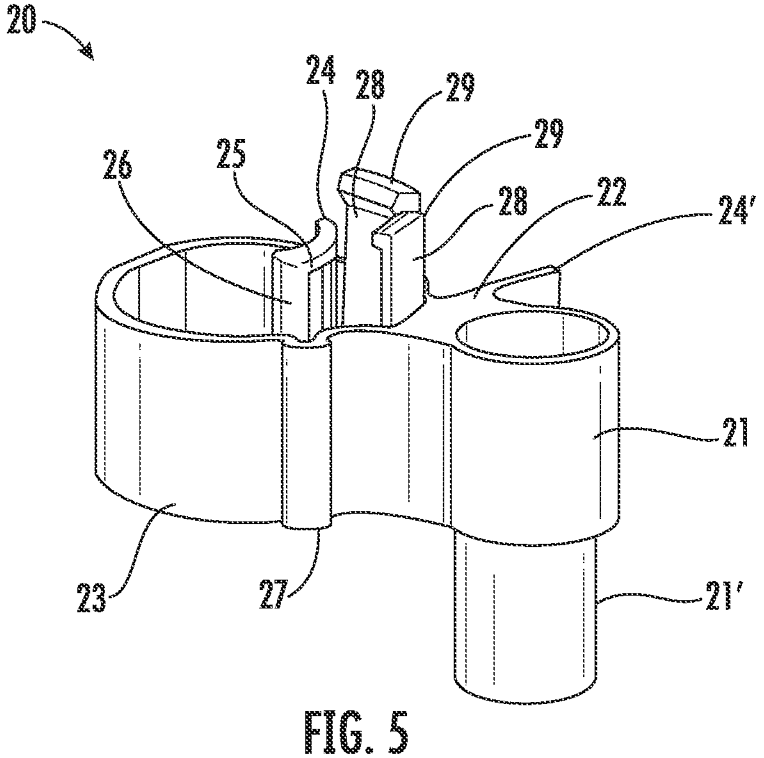
FIG. 5 is a perspective view of one embodiment of a retaining assembly of the vacuum shield assembly according to the present invention.
Figure 11:
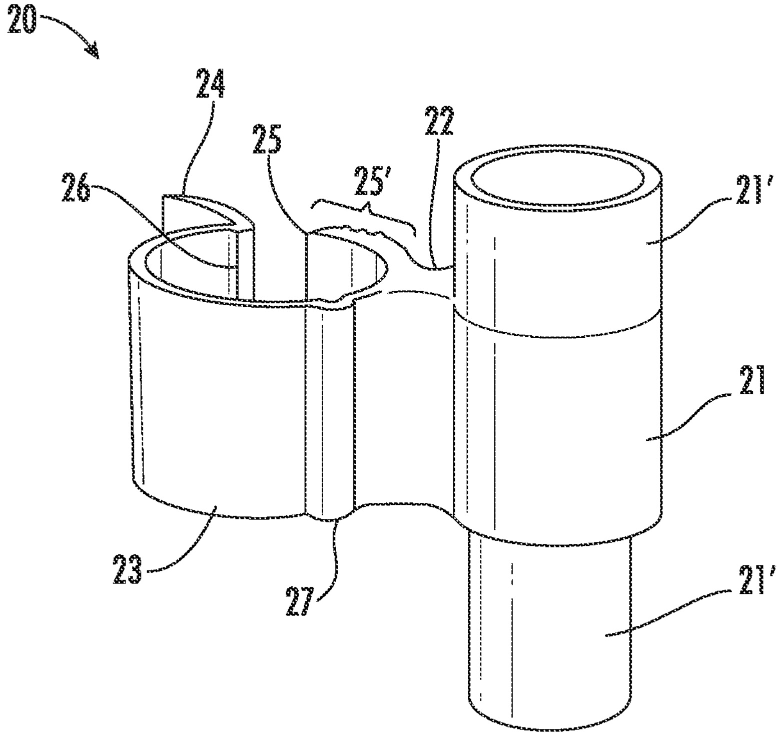
FIG. 11 is a perspective view of another embodiment of a retaining assembly of the vacuum shield assembly according to the present invention.

As seen in the illustrative embodiments of FIGS. 5 and 11, the retaining assembly 20 may comprise a retaining frame 23 connected to a retaining component 21. As mentioned above, a connecting portion 18 of the vacuum shield assembly 10 may be configured and dimensioned to correspond to the size of a retaining component 21 of the retaining assembly 20. As may be appreciated from FIG. 11, sometimes it may be beneficial to provide for a height adjustment for the point of connection between the connecting portion 18 of the shield body 11 and the retaining assembly 20. In such embodiments, the retaining component 21 may be provided with an upper section 21", which may at least partially raise the position of the shield body 11 relative to the point of attachment of the retaining assembly 20 to the oxygen supply tube or other related component of the existing mask.

Additional features of the present invention comprise providing a shield body 11 that may be configured and dimensioned to correspond to the geometry and/or size of the head and/or face of patient and/or the existing mask and its components. It is within the scope of the present invention that when the shield body 11 is disposed against the existing mask that a substantial portion of the edge 12 at least partially surround the existing mask. That is, the shield body 11, including the edge 12 of the perimeter, should define a profile or area that is at least equal to or even greater than the profile or area of the existing mask. As is perhaps best represented in FIG. 10, a lower segment 15 may be disposed on the lower part of the shield body 11, for example, below a lower perimeter 14 thereof. As such, exhaled air from the patient will be retained on an inside of the shield body 11, including above a lower segment 15. As an example, as is shown at least in FIGS. 4 and 9-10, the edge 12 may comprise a semi-ovoidal configuration. As is perhaps best shown in FIGS. 4 and 9, the edge 12 may also define a substantially flat side profile of the shield body 11. However, the shield body 11 may comprise other shapes to correspond to the shape of the existing mask. The lower segment 15 may be configured and dimensioned to accommodate the size and/or geometry of an oxygen supply tube of a BIPAP or CPAP mask, or the size and/or geometry of a nebulizer unit and/or components thereof.

The illustrative embodiment of FIGS. 6-9 and 11 show a retaining assembly 20 comprising a retaining component 21 and an upper section 21" thereof which provides for a vertical offset. The length of the upper section 21" may be configured and dimension according to preferences, type of existing mask, intended application, amount of height adjustment needed for the shield body 11, etc. These illustrative embodiments, both of the retaining component 21 and the upper section 21" comprise a substantially cylindrical configuration with approximately the same diameter. Conversely, as is in the illustrative embodiments of FIGS. 1-5, the retaining assembly 20 may be provided with a retaining component 21 without an upper section 21". It is within the scope of the present invention that the connecting portion 18 of the shield body 11 be attachable to the retaining component 21 and/or upper section 21" thereof. For example, the connecting component 18 may comprise a substantially cylindrical configuration, which may be configured and dimensioned to correspond to the size of an inside of a cylindrical retaining component 21 and/or upper section 21". Further to this example, and as is perhaps best shown in FIGS. 4 and 9, the outer diameter of the connecting component 18 may be at least partially smaller than the inner diameter of the retaining component 21 and/or upper section 21", such that the connecting component 18 may be inserted into the retaining component 21 and/or upper section 21". In at least one embodiment the retaining component 21 and upper section 21" may comprise the same diameter. Additionally, in such embodiments, both diameters of the connecting component 18, retaining component 21 and/or upper section 21" may be configured and dimensioned to enable a frictional resistance between corresponding surfaces such that the shield body 11 may be connected to the retaining assembly 20, and further, so that it may remain in place during periods of operation or use of the inventive vacuum shield assembly 10.

As may be perhaps best shown in the illustrative embodiments of FIGS. 2-5 and 7-11, the retaining component 21 of the retaining assembly 20 comprises a lower section 21'. The inside of the lower section 21' of the retaining component 21 should be disposed in fluid communication with the inside of the retaining component 21, the inside of the connecting portion 18 of the shield body 11, the inside of the upper section 21" of the retaining component, and/or the inside of the vacuum tube. Additionally, the lower section 21' of the retaining component 21 may be configured and dimensioned for attachment of the vacuum tube. By way of example only, the lower section 21' of the retaining component 21 may be provided with an outer diameter that is at least partially smaller to an inner diameter of the vacuum tube. As such, the vacuum tube may be attached to the outside of the lower section 21' of the retaining component 21, and may be disposed in fluid communication with an inside of the lower section 21' of the retaining component 21, the inside of the retaining component 21, an inside of the upper section 21" of the retaining component 21, and/or an inside of the connecting portion 18. This should enable a fluid communication between the vacuum tube and the shield body 11, including on an interior or inside thereof, which is perhaps best shown in FIG. 10. As such, activation of the vacuum tube will result in a negative pressure around the inside of the shield body 11. Such a negative pressure will result in at least a partial removal of the air on the inside of the shield body 11 and/or the surrounding area.

With reference to at least FIGS. 5 and 11, and as mentioned above, the retaining assembly 20 may be provided with a retaining frame 23. The retaining frame 23 may be connected to the retaining component 21, for example, via a transition structure 22. The retaining frame 23 is intended to attach the retaining assembly 20, and consequently the shield body 11 and vacuum tube, to a component of the existing mask. For example, such a component of the existing mask may include an oxygen supply tube of a BIPAP of CPAP mask. Also as an example, such a component of the existing mask may also include a nebulizing unit or a portion or component thereof. The retaining frame 23 should comprise an inner area, which may be selectively adjusted to securely retain the oxygen supply tube or nebulizing unit or component thereof. For example, the retaining frame 23 may comprise a substantially cylindrical configuration and/or two segments which may be connected to one another. A first closing structure 25 and a second closing structure 26 may be provided and may be cooperatively configured to form a closing mechanism or engagement that retains the oxygen supply tube or nebulizing unit. Also as an example, the first closing structure 25 and/or second closing structures 26 may be provided with a closing mechanism or related components that may enable such closing mechanism or engagement.

In the illustrative embodiments of FIGS. 1-11, a first closing structure 25 may be provided with a snap component whereas a second closing structure 26 may be provided with serrations 25'. The snap component and the serrations 25' may be cooperatively configured with one another to form a mating engagement, and allow a user or medical practitioner to selectively increase or decrease the inner area of the retaining frame 23. For example, the snap may be selectively disposed in any one of a plurality of serrations 25' along the length of one of the segments of the retaining frame 23. As used herein, a "snap" mechanism generally refers to a single-snap mechanism, or a multi-snap mechanism, i.e., an adjustable mechanism that may be selectively disposed into various size settings. As such, one single retaining assembly 20 may be used in connection with various oxygen supply tubs of different sizes and/or nebulizer units of different sizes. To further assist the user or medical practitioner in adjusting the inner area or opening of the retaining frame 23, one or more flaps 24 and/or 24' may be provided. The flaps 24 and/or 24' may be disposed or otherwise formed on the segments of the retaining frame 23, including around the first closing structure 25 and/or second closing structure 25. The flaps 24 and/or 24' may extend along the height of the retaining frame 23 and/or may comprise a size that corresponds to the size of the thumbs and/or fingers of a user or medical practitioner. Thus, selective movement of the flaps 24 and/or 24 will result in a corresponding movement of at least one of the segments of the retaining frame 23, and consequently movement of a corresponding closing structure 25 and/or 26. Although a retaining assembly 20 may be provided comprising two flaps 24 and 24', it is also possible to provide a retaining assembly 20 comprising only one flap 24 or one without any flaps.

As is perhaps best show in in FIG. 5, the retaining frame 23 may be provided with at least one retaining segment 28 configured to at least partially retain the nebulizing unit. For example, as shown in the illustrative embodiment of FIG. 3, two retaining segments 28 may be used to at least partially retain a middle section of a nebulizing unit. Further, each retaining segment(s) 28 may comprise latch 29 disposed around an upper end thereof. The latch(es) 29 may be configured to hold the top of the middle section of the nebulizing unit in place and at least partially reduce its movement in the vertical direction. As is also shown in the illustrative embodiment of FIG. 3, and also in other embodiments, the retaining frame 23 may be provided with a substantially cylindrical or semi-cylindrical configuration. Such configuration is advantageous to retain or otherwise attach the retaining assembly 20 to substantially cylindrical nebulizers or oxygen supply tubes.

With reference now to at least FIGS. 1-3 and 6-8, features of the present invention comprise providing a vacuum shield assembly 10 with a shield body 11 and a retaining assembly 20 collectively disposable into and out of an operative position and an inoperative position. As used herein, the "inoperative position" refers to a position of non-use of the vacuum shield assembly 10, and may include a storage position, an inactive position, a position where the vacuum shield assembly is not connected to external components, e.g., an oxygen supply tube, vacuum tube, nebulizer unit, face or head of a patient, etc. Conversely, as used herein, the "operative position" refers to an operational or otherwise active positon of the vacuum shield assembly 10. In the operative position, the shield body 11 should be connected to and disposed in fluid communication with the retaining assembly 20. As is shown at least in FIGS. 1-3 and 6-8, in the operative position, an interior or inside of the shield body 11 should be oriented toward the existing mask, which should already be disposed on the face and/or head of the patient. In the operative position, the vacuum tube, and/or connected vacuum source, should exert a negative pressure, which should result on a corresponding exerted negative pressure around the shield body 11 and the surrounding area. It is contemplated that in the operative position, the negative pressure exerted around the inside or interior of the shield body 11, and/or above the lower segment 15, should be sufficient to at least partially extract the exhaled air form the patient. Also, the lower segment 15, along with the interior or inside of the shield body 11, is intended to at least partially retain exhaled air between the face of the patient and/or existing mask, and the shield body 11. As such, movement of the exhaled patient air outside of the area surrounding the shield body 11 may be at least partially reduced, such that, the negative pressure of the vacuum tube, should result on an efficient removal of the exhaled air.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A vacuum shield assembly for a patient wearing a medical mask, the vacuum shield assembly comprising:

a shield body having a first opening extending from a bottom portion of the shield body and configured to couple to a vacuum tube and the shield body having a profile configured and dimensioned to extend beyond a profile of the medical mask to allow exhaled air from the patient to be retained on an inside portion of the shield body; and a retaining assembly having a plurality of connecting arms, a first connecting arm having a first coupling configured to couple the first opening on the bottom portion of the shield body to the vacuum tube, and a second connecting arm having a second coupling spaced apart from the first coupling and having a retaining segment extending therefrom and the second coupling configured to couple around a supply tube of the medical mask or a nebulizer unit, the retaining assembly configured to suspend the shield body from the bottom portion and completely over the medical mask; and wherein the vacuum tube is configured to exert a negative pressure between the medical mask and the inside portion of the shield body when coupled to the first opening.

2. The vacuum shield assembly as recited in claim 1 wherein the shield body is dimensioned and configured to at least partially surround the medical mask.

3. The vacuum shield assembly as recited in claim 1 further comprising a second opening disposed substantially on a middle section of the shield body.

4. The vacuum shield assembly as recited in claim 1 further comprising a second opening disposed substantially on a middle section of the shield body.

5. The vacuum shield assembly as recited in claim 4 wherein the second opening is configured and dimensioned to receive a connecting segment of the medical mask.

6. The vacuum shield assembly as recited in claim 4 wherein the medical mask comprises a bag-valve-mask (BVMV) resuscitator mask or a demand-valve resuscitator (DVR) mask.

7. The vacuum shield assembly as recited in claim 6 further comprising a vacuum attachment configured to substantially define a seal between the second opening and a connecting segment of the bag-valve-mask (BVM) resuscitator mask or the demand-valve resuscitator (DVR) mask.

8. The vacuum shield assembly as recited in claim 1 wherein an operative position comprises the shield body positioned adjacent to and facing the medical mask, and the vacuum tube is configured to exert a negative pressure on an inside of the shield body at least partially removing patient exhaled air between the shield body and the medical mask when the vacuum tube is coupled to the first opening.

9. The vacuum shield assembly as recited in claim 1 wherein a concave configuration of the shield body is structured to define a space around the supply tube or a nebulizer unit of the medical mask.

10. A vacuum shield assembly for a patient wearing a medical mask, the vacuum shield assembly comprising:

a shield body having a first opening and a second opening, the first opening is configured to couple to a vacuum tube, the shield body configured and dimensioned to at least partially surround the medical mask; and a vacuum attachment having a segmented cover that is secured over the second opening, wherein the second opening is configured and dimensioned to receive a connecting segment of a bag-valve-mask resuscitator (BVM) mask or a demand-valve resuscitator (DVR) mask, and the segmented cover of the vacuum attachment is configured to partially open to substantially form a seal between the second opening and the connecting segment of the bag-valve-mask resuscitator (BVM) mask or a demand-valve resuscitator (DVR) mask, and the segmented cover providing a seal over the second opening when the second opening is not being used;

a retaining assembly having a plurality of connecting arms, a first connecting arm having a first coupling configured to couple the first opening on the bottom portion of the shield body to the vacuum tube, and a second connecting arm having a second coupling spaced apart from the first coupling and having a retaining segment extending therefrom and the second coupling configured to couple to the connecting segment of the BVM or DVR.

11. The vacuum shield assembly as recited in claim 10 wherein the vacuum attachment comprises a silicone material.

12. The vacuum shield assembly as recited in claim 10 wherein the vacuum attachment comprises a substantially circular shape configured and dimensioned to correspond to a geometry and size of the second opening.

13. The vacuum shield assembly as recited in claim 10 wherein the vacuum attachment comprises a grommet configuration.

14. The vacuum shield assembly as recited in claim 13 wherein the segmented cover comprises a plurality of adjacently disposed segments cooperatively disposable into and out of an open position and a closed position.

15. The vacuum shield assembly as recited in claim 14 wherein each one of the plurality of segments comprises a substantially triangular shape.

16. The vacuum shield assembly as recited in claim 10 wherein the segmented cover includes a plurality of reinforcement ribs.

* * * * *